United States Patent
Chen et al.

(10) Patent No.: US 9,120,818 B2
(45) Date of Patent: Sep. 1, 2015

(54) PROCESS AND INTERMEDIATES FOR PREPARING MACROLACTAMS

(75) Inventors: Cheng Chen, Plainsboro, NJ (US); Jongrock Kong, Princeton, NJ (US); Guy Humphrey, Hillsborough, NJ (US); Sarah Dolman, Jersey City, NJ (US); Hongmei Li, Edison, NJ (US); Matthew T. Tudge, Chatham, NJ (US); Kelvin Yong, Lyndhurst, NJ (US); Bangping Xiang, Plainsboro, NJ (US); Michael Zacuto, Jersey City, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/993,541

(22) PCT Filed: Dec. 13, 2011

(86) PCT No.: PCT/US2011/064521
§ 371 (c)(1),
(2), (4) Date: Jun. 12, 2013

(87) PCT Pub. No.: WO2012/082672
PCT Pub. Date: Jun. 21, 2012

(65) Prior Publication Data
US 2013/0274463 A1    Oct. 17, 2013

Related U.S. Application Data

(60) Provisional application No. 61/422,907, filed on Dec. 14, 2010.

(51) Int. Cl.
| | | |
|---|---|---|
| *C07D 207/02* | (2006.01) | |
| *C07D 403/12* | (2006.01) | |
| *C07D 498/16* | (2006.01) | |
| *C07C 271/22* | (2006.01) | |
| *C07C 271/24* | (2006.01) | |
| *C07C 309/80* | (2006.01) | |
| *C07C 309/85* | (2006.01) | |
| *C07C 311/51* | (2006.01) | |
| *C07D 207/16* | (2006.01) | |
| *C07D 498/18* | (2006.01) | |
| *C07D 209/44* | (2006.01) | |
| *C07K 5/062* | (2006.01) | |
| *C07C 271/56* | (2006.01) | |
| *C07C 311/47* | (2006.01) | |

(52) U.S. Cl.
CPC ............ *C07D 498/16* (2013.01); *C07C 271/22* (2013.01); *C07C 271/24* (2013.01); *C07C 271/56* (2013.01); *C07C 309/80* (2013.01); *C07C 309/85* (2013.01); *C07C 311/47* (2013.01); *C07C 311/51* (2013.01); *C07D 207/16* (2013.01); *C07D 209/44* (2013.01); *C07D 403/12* (2013.01); *C07D 498/18* (2013.01); *C07K 5/06034* (2013.01); *C07C 2101/02* (2013.01)

(58) Field of Classification Search
CPC ............................ C07D 207/02; C07D 403/12
USPC .................................. 540/458; 548/465, 536
See application file for complete search history.

(56) References Cited

U.S. PATENT DOCUMENTS 7,470,664 B2    12/2008    Holloway et al.

FOREIGN PATENT DOCUMENTS

| WO | 03099274 A1 | 12/2003 |
|---|---|---|
| WO | 2006102087 A2 | 9/2006 |
| WO | 2006119061 A2 | 9/2006 |
| WO | 2007015787 A1 | 2/2007 |
| WO | 2007015855 A1 | 2/2007 |
| WO | 2007016441 A1 | 2/2007 |
| WO | 2007131966 A1 | 11/2007 |
| WO | 2007148135 A1 | 12/2007 |
| WO | 2008051477 A2 | 5/2008 |
| WO | 2008051514 A2 | 5/2008 |
| WO | 2008057208 A2 | 5/2008 |
| WO | 2008057209 A1 | 5/2008 |
| WO | 2009010804 A1 | 1/2009 |
| WO | 2009108507 A1 | 9/2009 |
| WO | 2009134624 A1 | 11/2009 |
| WO | 2010011566 A1 | 1/2010 |

OTHER PUBLICATIONS

Balsano, "Recent Advances in Antiviral Agents: Established and Innovative Therapies for Viral Hepatitis", Mini-Reviews in Medicinal Chemistry, 2008, pp. 307-318, vol. 8.
DeFrancesco et al., "Approaching a New Era for Hepatitis C Virus Therapy: Inhibitors of the NS3-4A Serine Protease and the NS5B RNA-Dependent RNA Polymerase", Antiviral Research, 2003, pp. 1-16, vol. 58.

(Continued)

*Primary Examiner* — Bruck Kifle
(74) *Attorney, Agent, or Firm* — Anna Cocuzzo; Henry P. Wu

(57) ABSTRACT

The present invention relates to macrolactam compounds, intermediates useful in the preparation of macrolactams, methods for preparing the intermediates, and methods for preparing and modifying macrolactams. One use of the compounds and methods described herein is in the production of macrolactam compounds able to inhibit HCV NS3 protease activity. An example of an HCV inhibitory compound that can be synthesized using the procedures described herein is Compound A and derivative thereof.

20 Claims, No Drawings

(56) References Cited

OTHER PUBLICATIONS

Liverton et al., "MK-7009, A Potent and Selective Inhibitor of Hepatitis C Virus NS3/4A Protease", Antimicrobial Agents and Chemotherapy, 2009, pp. 305, vol. 54, No. 1.
Liverton et al., "Molecular Modeling Based Approach to Potent P2-P4 Macrocyclic Inhibitors of Hepatitis C NS3/4A Protease", J Amer Chem Soc, 2008, pp. 4607-4609, vol. 130.
McCauley et al., "Discovery of Vaniprevir (NK-7009), A Macrocyclic Hepatitis C Virus NS3/4a Protease Inhibitor", J Med Chem, 2010, pp. 2443-2463, vol. 53, No. 6.
McCauley et al., "Abstracts of Papers, Discovery of MK-7009: A Novel Macrocyclic HCV NS3/4A Protease Inhibitor", 235th ACS National Meeting, New Orleans, LA, United States, Apr. 2008.
Ronn et al., "New Developments in The Discovery of Agents to Treat Hepatitis C", Current Topics in Medicinal Chemistry, 2008, pp. 533-562, vol. 8.
Sheldon et al., "Novel Protease and Polymerase Inhibitors for the Treatment of Hepatitis C Virus Infection", Expert Opinion Investigational Drugs, 2007, pp. 1171-1181, vol. 16, No. 8.
Zacuto et al., "Preparation of 4-Allyisoindoline via a Kumada Coupling With Allylmagnesium Chloride," Organic Process Research 2011, pp. 158, vol. 15, No. 1.

PROCESS AND INTERMEDIATES FOR PREPARING MACROLACTAMS

FIELD OF THE INVENTION

The present invention relates to method and compounds that can be used to produce macrolactams, and modify macrolactams. One use of the methods and compounds described herein is in the production of macrolactam compounds able to inhibit HCV NS3 protease activity.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein. NS4A provides a cofactor for NS3 activity.

Potential treatments for HCV infection have been discussed in different references including Balsano, *Mini Rev. Med. Chem.* 8(4):307-318, 2008, Rönn et al., *Current Topics in Medicinal Chemistry* 8: 533-562, 2008, Sheldon et al., *Expert Opin. Investig. Drugs* 16(8):1171-1181, 2007, and De Francesco et al., *Antiviral Research* 58:1-16, 2003.

Examples of publications describing macrolactam compounds able to inhibit HCV protease activity include: Holloway et al., U.S. Pat. No. 7,470,664, Harper et al., WO2010011566; Liverton et al., WO2009134624; McCauley et al., WO2009108507; Liverton et al., WO2009010804; Liverton et al., WO2008057209; Liverton et al., WO2008051477; Liverton et al., WO2008051514; Liverton et al., WO2008057208; Crescenzi et al., WO2007148135; Di Francesco et al., WO2007131966; Holloway et al., WO2007015855; Holloway et al., WO2007015787; Holloway et al., WO2007016441; Holloway et al., WO2006119061; Liverton et al., *J. Am. Chem. Soc.*, 130: 4607-4609, 2008; McCauley et al., *Abstracts of Papers*, 235th *ACS National Meeting*, New Orleans, La., United States, Apr. 6-10, 2008; Liverton et al., *Antimicrobial Agents and Chemotherapy* 54:305-311, 2009 (published online); and McCauley et al., *Journal of Medicinal Chemistry*, 53(6):2443-2463, 2010.

SUMMARY OF THE INVENTION

The present invention relates to macrolactam compounds, intermediates useful in the preparation of macrolactams, methods for preparing the intermediates, and methods for preparing and modifying macrolactams. One use of the compounds and methods described herein is in the production of macrolactam compounds able to inhibit HCV NS3 protease activity. An example of an HCV inhibitory compound that can be synthesized using the procedures described herein is Compound A and derivatives thereof. Compound A has the following structure:

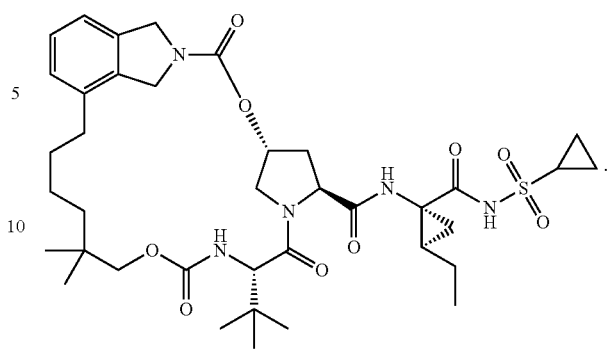

Thus, a first aspect of the invention is directed to a compound selected from the group consisting of:

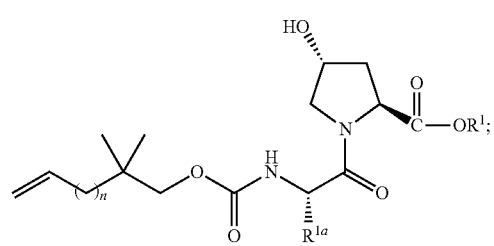
(Formula I)

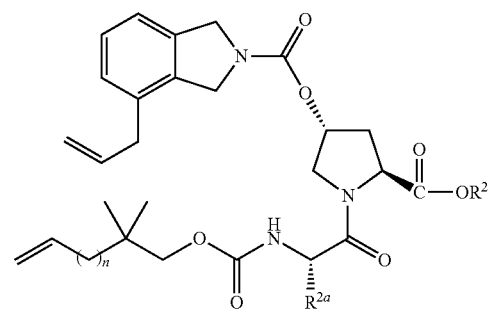
(Formula II)

or a salt thereof;

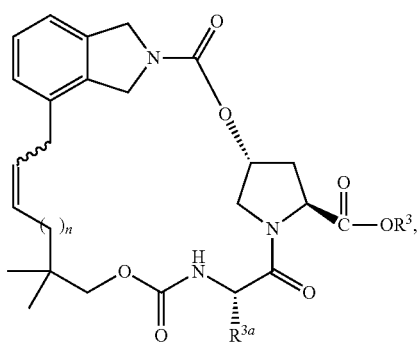
(Formula III)

or a salt thereof;

(Compound 6A)

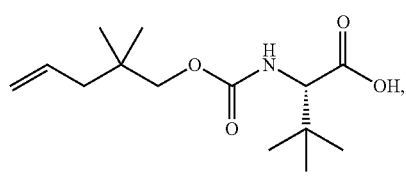

or a salt thereof, (Compound 3)

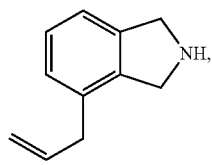

or a salt thereof;

(Compound A-2)

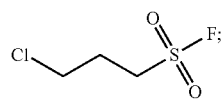

(Compound A-4)

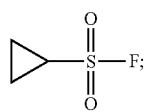

(Compound A-10)

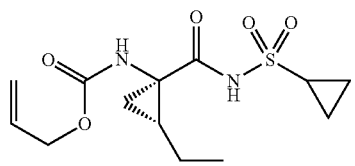

or a salt thereof; and (Compound B-6)

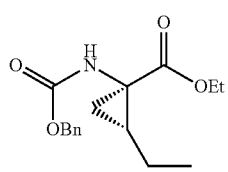

or a salt thereof;

wherein the different groups are described herein. (For example, see section I. Intermediates infra) Salts of Formula II or III compounds can readily be produced from the corresponding carboxylic acid (i.e., $R^2$ or $R^3$ is hydrogen).

Another aspect of the present invention is directed to a method of making a compound of Formula II or salt thereof, comprising the step of coupling a compound of Formula I with Compound 3 or salt thereof.

Another aspect is directed to a method of making a compound of (Formula IV)

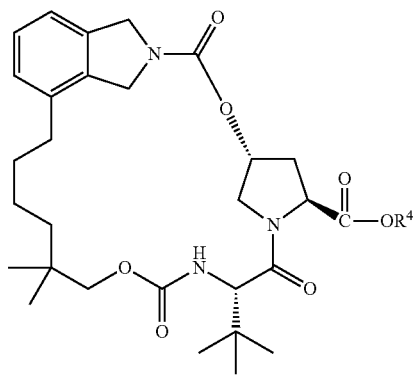

or salt thereof, comprising the step of ring closure and hydrogenation of a compound of Formula II or salt thereof to form a compound of Formula IV or salt thereof, Formula IV salts can readily be produced from the corresponding carboxylic acid (i.e., $R^4$).

Another aspect is directed to a method of making Compound A, or a pharmaceutical acceptable salt thereof, comprising the steps of:

a) making a compound of Formula IV or salt thereof comprising the step of ring closure and hydrogenation of a compound of Formula II or salt thereof to form the compound of Formula IV or salt thereof;

b) hydrolyzing the compound of Formula IV or salt thereof to form (Compound 11)

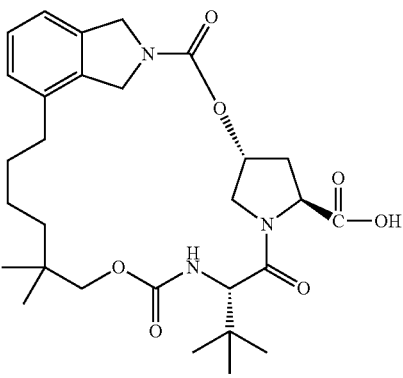

or salt thereof;

c) coupling Compound 11 or salt thereof to (Compound A-11)

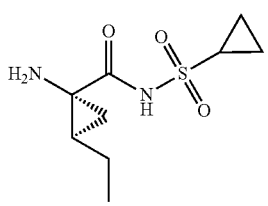

or salt thereof, to form Compound A or salt thereof, and d) optionally converting compound A or salt thereof into a pharmaceutically acceptable salt.

Another aspect of the present invention is directed to a method of making Compound 3 or salt thereof comprising the step of:

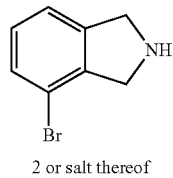 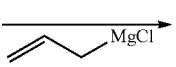

2 or salt thereof

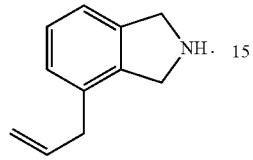

3

Another aspect is directed to a method of making the Compound A-8, comprising the following step:

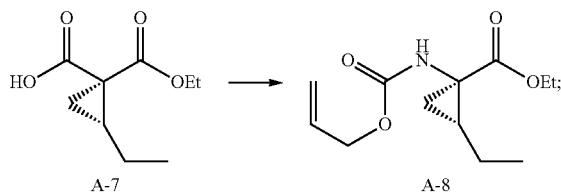

or salts thereof. Reference to salts thereof indicates Compounds A-7 and A-8 may be provided as a salt.

Another aspect is directed to a method of Compound A-11 comprising:

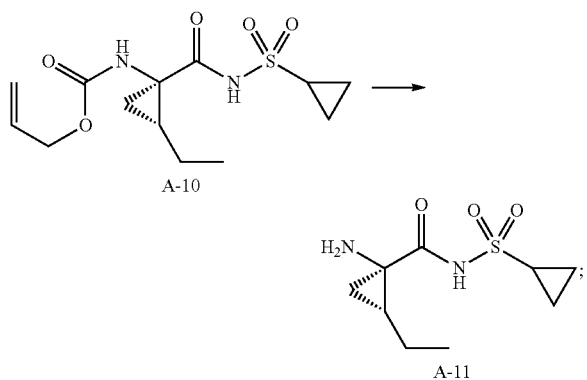

or salts thereof. Reference to salts thereof indicates Compounds A-10 and A-11 may be provided as a salt.

Another aspect is directed to a method making Compound A or salt thereof comprising the step of coupling

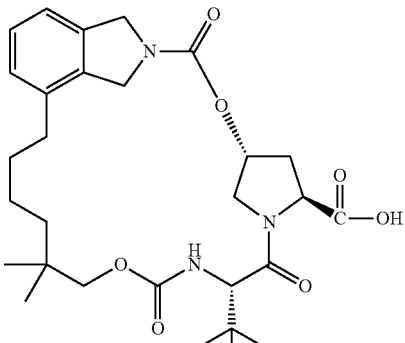

or salt thereof, to

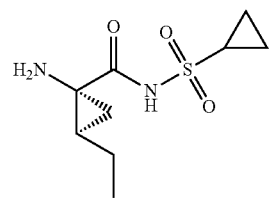

or salt thereof, to form Compound A or salt thereof, wherein the reaction comprises the use of a coupling reagent and pyridine or a pyridine derivative.

Other embodiments, aspects and features of the present invention are either further described herein or will be apparent from the ensuing description, examples and appended claims.

DETAILED DESCRIPTION OF THE INVENTION

The methods and intermediates described herein can be used to synthesize macrolactams such as Compound A and compounds varying from Compound A by one or more functional groups present in Compound A. Functional groups that can be modified include a different heterocycle group, a different alkyl in place of the t-butyl group, and alteration of the cyclopropylsulfonyl functional group (e.g., with an ethyl group replacing the ethylene and/or a methylcyclopropyl group replacing the cyclopropyl group). An example of a structure covering some derivatives of Compound A is:

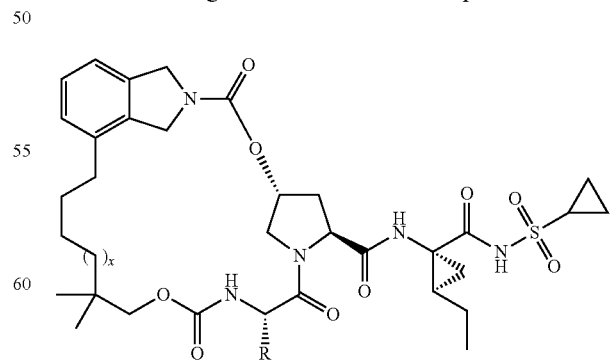

wherein x is 0 to 5, and R is $C_{1-6}$ alkyl or $C_3$-$C_8$ cycloalkyl. Preferably, x is 0 to 2, more preferably 1. Preferably R is either t-butyl or cyclohexyl.

Different intermediates and synthesis protocols are illustrated herein where Compound A was ultimately obtained. However, it is understood that based on the guidance provided herein other macrolactams can be produced using appropriate intermediates and by adding or modifying different functional groups. Examples of different macrolactams having different functional groups are provided in Holloway et al., U.S. Pat. No. 7,470,664; Harper et al., WO2010011566; Liverton et al., WO2009134624; McCauley et al., WO2009108507; Liverton et al., WO2009010804; Liverton et al., WO2008057209; Liverton et al., WO2008051477; Liverton et al., WO2008051514; Liverton et al., WO2008057208; Crescenzi et al., WO2007148135; Di Francesco et al., WO2007131966; Holloway et al., WO2007015855; Holloway et al., WO2007015787; Holloway et al., WO2007016441; Holloway et al., WO2006119061; Liverton et al., *J. Am. Chem. Soc.*, 130: 4607-4609, 2008; McCauley et al., *Abstracts of Papers, 235th ACS National Meeting*, New Orleans, La., United States, Apr. 6-10, 2008; Liverton et al., *Antimicrobial Agents and Chemotherapy* 54:305-311, 2009 (published online); and McCauley et al., *Journal of Medicinal Chemistry*, 53(6):2 443-2463, 2010.

McCauley et al., *Abstracts of Papers, 235th ACS National Meeting*, New Orleans, La., United States, Apr. 6-10, 2008; Liverton et al., *Antimicrobial Agents and Chemotherapy* 54:305-311, 2009 (published online); McCauley et al., *Journal of Medicinal Chemistry*, 53(6):2443-2463, 2010; Holloway et al., U.S. Pat. No. 7,470,664; Holloway et al., WO2007015855; and Holloway et al., WO2007015787 describe Compound A and alternative methods for making Compound A.

Macrolactam compounds able to inhibit HCV activity have different uses including inhibiting HCV activity in vivo, inhibiting HCV activity in vitro, and inhibiting HCV NS3 enzymatic activity. In vivo inhibition of HCV activity can be used for therapeutic applications. Inhibiting HCV activity in vitro has different applications including being used to obtain HCV resistant mutants, further characterizing the ability of a functional group to inhibit HCV replicon or enzymatic activity, and studying HCV replication or protease activity.

I. Intermediates

Different compounds that can be used to produce marcolactam compounds, such as Compound A, are described herein including this section and elsewhere in the present application. In a first aspect directed to different intermediates, the compound is selected from the group consisting of:

(Formula I)

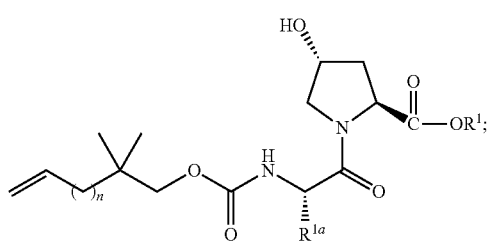

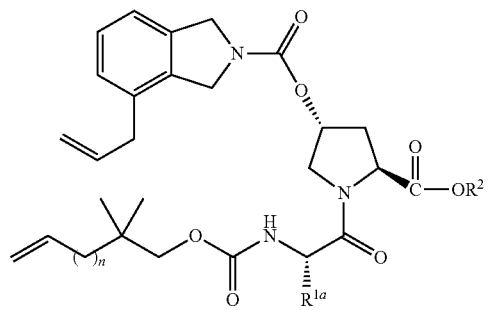

(Formula II)

or a salt thereof;

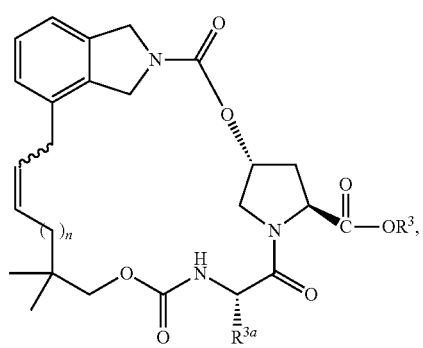

(Formula III)

or a salt thereof;

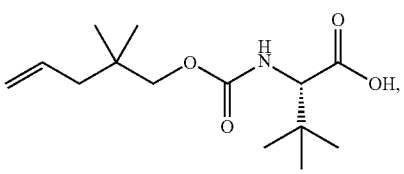

(Compound 6A)

or a salt thereof,

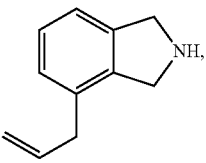

(Compound 3)

or a salt thereof;

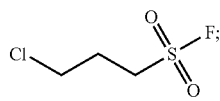

(Compound A-2)

-continued (Compound A-4)

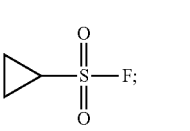

(Compound A-10)

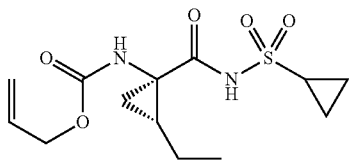

or a salt thereof; and (Compound B-6)

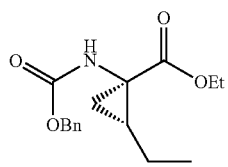

or a salt thereat
wherein $R^1$ is either a $C_{1-6}$ alkyl, $C_3$-$C_8$ cycloalkyl, or Aryl;
$R^2$ and $R^3$ are each either H, $C_{1-6}$ alkyl, $C_3$-$C_8$ cycloalkyl, or Aryl;
$R^{1a}$, $R^{2a}$, and $R^{3a}$ are each either $C_{1-6}$ alkyl or $C_3$-$C_8$ cycloalkyl; and
n is 0-5.

Aryl is either phenyl, substituted phenyl, naphthyl, or substituted naphthyl, provided that substituted phenyl and substituted naphthyl each have 1 to 5 substituents independently selected from the group consisting of:
(1) $C_{1-6}$ alkyl,
(2) $C_{1-6}$ alkyl substituted with OH, O—$C_{1-6}$ alkyl, O—$C_{1-6}$ haloalkyl, CN, NO$_2$, N(R$^A$)R$^B$, C(O)N(R$^A$)R$^B$, C(O)R$^A$, CO$_2$R$^A$, SR$^A$, S(O)R$^A$, SO$_2$R$^A$, SO$_2$N(R$^A$)R$^B$, N(R$^A$)C(O)R$^B$, N(R$^A$)CO$_2$R$^B$, N(R$^A$)SO$_2$R$^B$, N(R$^A$)SO$_2$N(R$^A$)R$^B$, OC(O)N(R$^A$)R$^B$, N(R$^A$)C(O)N(R$^A$)R$^B$, or N(R$^A$)C(O)C(O)N(R$^A$)R$^B$,
(3) O—$C_{1-6}$ alkyl,
(4) $C_{1-6}$ haloalkyl,
(5) O—$C_{1-6}$ haloalkyl,
(6) OH,
(7) halogen,
(8) CN,
(9) NO$_2$,
(10) N(R$^A$)R$^B$,
(11) C(O)N(R$^A$)R$^B$,
(12) C(O)R$^A$,
(13) C(O)—$C_{1-6}$haloalkyl,
(14) C(O)OR$^A$,
(15) OC(O)N(R$^A$)R$^B$,
(16) SR$^A$,
(17) S(O)R$^A$,
(18) SO$_2$R$^A$,
(19) SO$_2$N(R$^A$)R$^B$,
(20) N(R$^A$)SO$_2$R$^B$,
(21) N(R$^A$)SO$_2$N(R$^A$)R$^B$,
(22) N(R$^A$)C(O)R$^B$,
(23) N(R$^A$)C(O)N(R$^A$)R$^B$,
(24) N(R$^A$)C(O)C(O)N(R$^A$)R$^B$, or
(25) N(R$^A$)CO$_2$R$^B$; and
$R^A$ and $R^B$ are each independently H or $C_{1-6}$ alkyl.

In a second aspect, the compound is:

(Formula I)

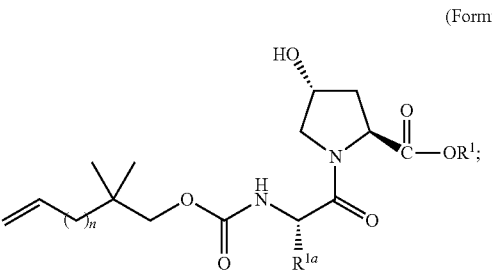

where a preferred subclass is:

(Formula Ia)

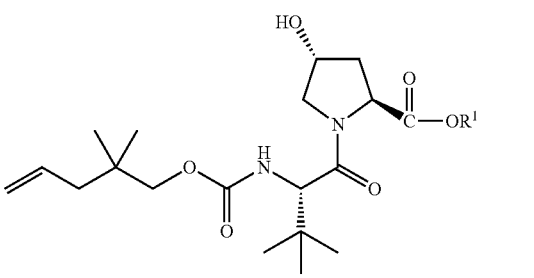

wherein $R^1$, $R^{1a}$, and n are as defined is the first aspect.

In a first embodiment, $R^1$ is either $C_{1-6}$ alkyl, $C_3$-$C_8$ cycloalkyl, phenyl or naphthyl.

In a second embodiment, $R^1$ is a $C_{1-6}$ alkyl or $C_3$-$C_8$ cycloalkyl.

In a third embodiment, $R^1$ is a $C_{1-6}$ alkyl.

In a fourth embodiment, $R^{1a}$ is either t-butyl or cyclohexyl, and $R^1$ is as provided in the first aspect or embodiment 1-3.

In a fifth embodiment, $R^{1a}$ is t-butyl, and $R^1$ is as provided in the first aspect or any of embodiments 1-3.

In a sixth embodiment, n is 0-2, and $R^1$ and $R^{1a}$ are as provided in the first aspect or any of embodiments 1-4.

In a seventh embodiment, n is 1, and $R^1$ and $R^{1a}$ are as provided in the first aspect or any of embodiments 1-5.

In an eighth embodiment, the Formula I compound is:

(Compound 7)

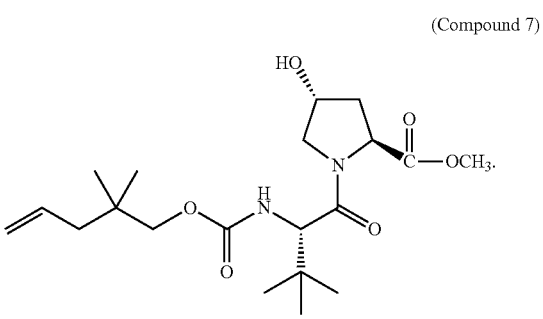 [SMILES: C=CCC(C)(C)COC(=O)N[C@H](C(=O)N1C[C@H](O)C[C@H]1C(=O)OC)C(C)(C)C]

In a third aspect, the compound is:

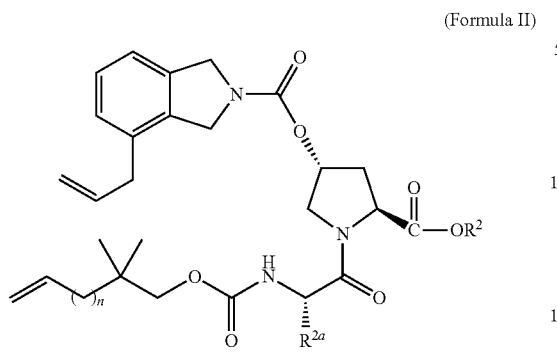

(Formula II)

or a salt thereof; where a preferred subclass is:

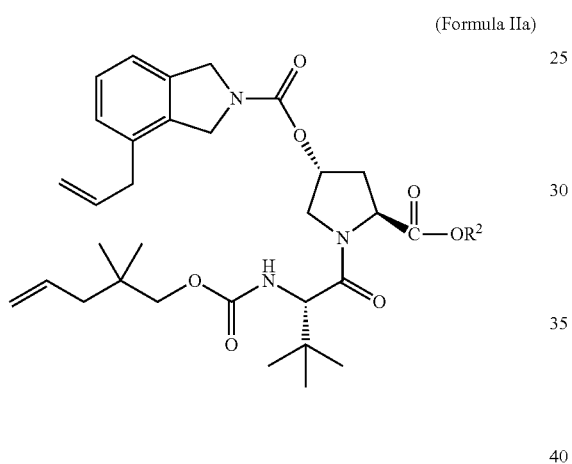

(Formula IIa)

or a salt thereof;
wherein $R^2$, $R^{2a}$, and n are as defined in the first aspect. Salts can be readily produced when $R^2$ is H.

In a first embodiment, $R^2$ is either H, $C_{1-6}$ alkyl, $C_3$-$C_8$ cycloalkyl, phenyl or naphthyl.

In a second embodiment, $R^2$ is either H, $C_{1-6}$ alkyl or $C_3$-$C_8$ cycloalkyl.

In a third embodiment, $R^2$ is $C_{1-6}$ alkyl.

In a fourth embodiment, the compound is a salt of Formula II or IIa. In a further embodiment, the salt is either potassium, sodium, lithium, a primary amine ($NH_3^+$—$R^C$), a secondary amine ($NH_2^+$—$(R^C)_2$), or a tertiary amine ($NH^+$—$(R^C)_3$), wherein each $R^C$ is independently $C_{1-6}$ alkyl, $C_3$-$C_8$ cycloalkyl, or Aryl; provided that two $R^C$ can together form a three to eight membered heterocyclic group containing $NH^+$ and —$(CH_2)_n$—, where n is 2-7, preferably 5 or 6.

In a fifth embodiment, $R^{2a}$ is either t-butyl or cyclohexyl, and $R^2$ is as provided in the first aspect or any of embodiments 1-4.

In a sixth embodiment, $R^{2a}$ is t-butyl, and $R^2$ is as provided in the first aspect or any of embodiments 1-4.

In a seventh embodiment, n is 0-2, and $R^{2a}$ and $R^2$ are as provided in the first aspect or any of embodiments 1-6.

In an eighth embodiment, n is 1, and $R^2$ and $R^{2a}$ are as provided in the first aspect or any of embodiments 1-6.

In a ninth embodiment, the compound is

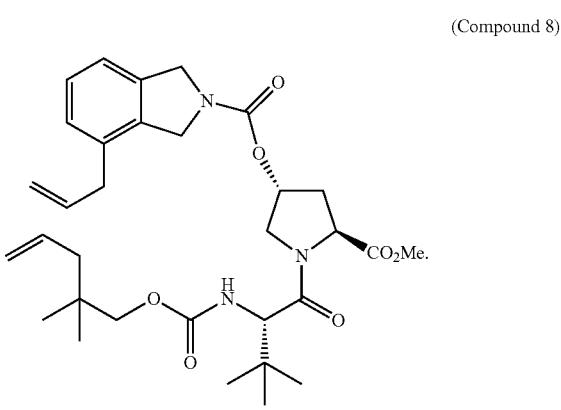 [SMILES: C=CCc1cccc2c1CN(C(=O)O[C@@H]1C[C@@H](C(=O)OC)N(C(=O)[C@@H](NC(=O)OCC(C)(C)CC=C)C(C)(C)C)C1)C2]

(Compound 8)

In a tenth embodiment, the compound is:

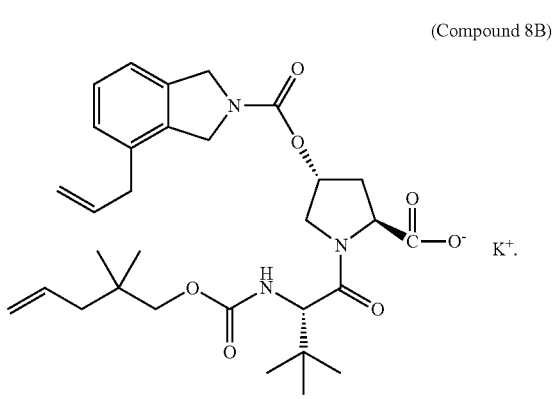 [SMILES: C=CCc1cccc2c1CN(C(=O)O[C@@H]1C[C@@H](C(=O)[O-])N(C(=O)[C@@H](NC(=O)OCC(C)(C)CC=C)C(C)(C)C)C1)C2]

(Compound 8B)

In an eleventh embodiment, the compound is:

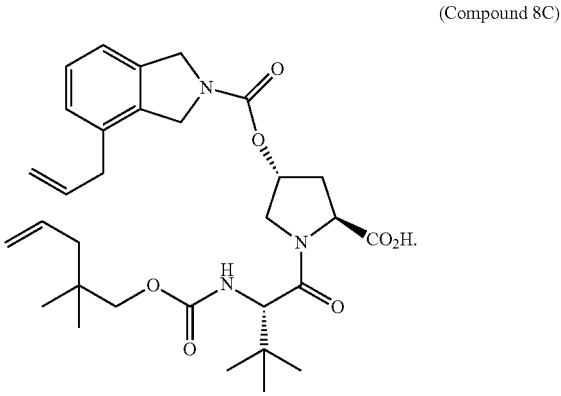 [SMILES: C=CCc1cccc2c1CN(C(=O)O[C@@H]1C[C@@H](C(=O)O)N(C(=O)[C@@H](NC(=O)OCC(C)(C)CC=C)C(C)(C)C)C1)C2]

(Compound 8C)

In a fourth aspect, the compound is:

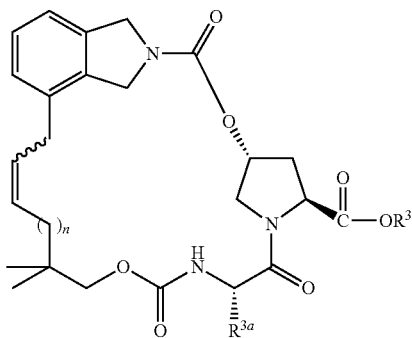
(Formula III)

or a salt thereof, where a preferred subclass is

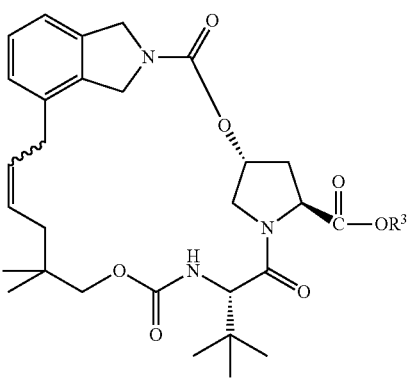
(Formula IIIa)

or salt thereof;
wherein $R^{3a}$, $R^3$, and n are as defined in the first aspect. Salts can be readily produced when $R^3$ is H. Compounds of Formula III and IIIa include both the cis and trans configuration. The methods described herein provide a mixture of cis and trans.

In a first embodiment, $R^3$ is either H, $C_{1-6}$ alkyl, $C_3$-$C_8$ cycloalkyl, phenyl or naphthyl.

In a second embodiment, $R^3$ is either H, $C_{1-6}$ alkyl or $C_3$-$C_8$ cycloalkyl.

In a third embodiment, $R^3$ is $C_{1-6}$ alkyl.

In a fourth embodiment, the compound is a salt of Formula III or IIIa. In a further embodiment, the salt is either potassium, sodium, lithium, a primary amine ($NH_3^+$—$R^C$), a secondary amine ($NH_2^+$—($R^C$)$_2$), or a tertiary amine ($NH^+$—($R^C$)$_3$); wherein each $R^C$ is independently $C_{1-6}$ alkyl, $C_3$-$C_8$ cycloalkyl, or Aryl; provided that two $R^C$ can together form a three to eight membered heterocyclic group containing $NH^+$ and —($CH_2$)$_n$—, where n is 2-7, preferably 5 or 6.

In a fifth embodiment, $R^{3a}$ is either t-butyl or cyclohexyl, and $R^3$ is as provided in the first aspect or any of embodiments 1-4.

In a sixth embodiment, $R^{3a}$ is t-butyl, and $R^3$ is as provided in the first aspect or any of embodiments 1-4.

In a seventh embodiment, n is 0-2, and $R^{3a}$ and $R^3$ are as provided in the first aspect or any of embodiments 1-6.

In an eighth embodiment, n is 1, and $R^3$ and $R^{3a}$ are as provided in the first aspect or any of embodiments 1-6.

In a ninth embodiment, the Formula III compound is

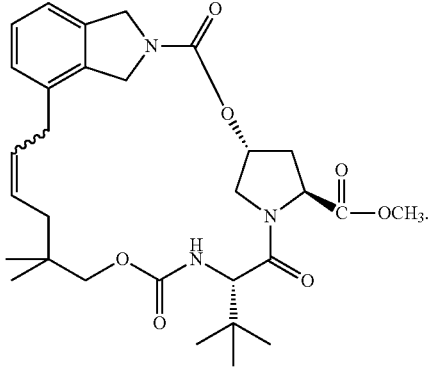
(Compound 9)

In a fifth aspect, the compound is:

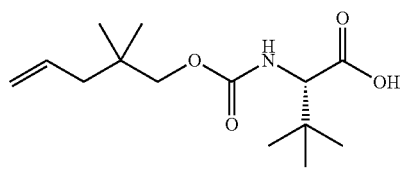
(Compound 6A)

or a salt thereof. In a further embodiment, the salt is either potassium, sodium, lithium, a primary amine ($NH_3^+$—$R^C$), a secondary amine ($NH_2^+$—($R^C$)$_2$), or a tertiary amine ($NH^+$—($R^C$)$_3$); wherein each $R^C$ is independently $C_{1-6}$ alkyl, $C_3$-$C_8$ cycloalkyl, or Aryl; provided that two $R^C$ can together form a three to eight membered heterocyclic group containing $NH^+$ and —($CH_2$)$_n$—, where n is 2-7, preferably 5 or 6. In a further embodiment, the compound is a cyclohexylamine or dicyclohexylamine salt of Compound 6A.

In a sixth aspect, the compound is:

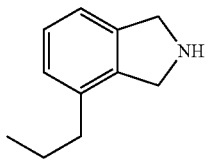
(Compound 3)

or a salt thereof. In an embodiment, the salt is either HCl, HBr, HI, $H_3PO_4$, $H_2SO_4$, TsOH (para-toluenesulfonic acid), MsOH (methanesulfonic acid), benzenesulfonic acid, AcOH, $Cl_3CCO_2H$, $Cl_2CHCO_2H$, $ClCH_2CO_2H$, or $CF_3CO_2H$.

In a seventh aspect, the compound is:

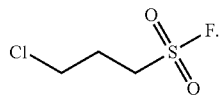
(Compound A-2)

In an eighth aspect, the compound is:

(Compound A-4)

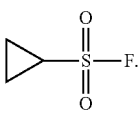

In a ninth aspect, the compound is:

(Compound A-10)

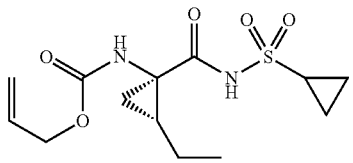

or a salt thereof.

In a tenth aspect, the compound is:

(Compound B-6)

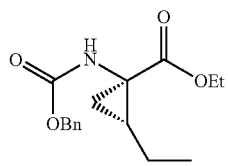

or a salt thereof.

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

The term "alkyl" refers to a monovalent straight or branched chain, saturated aliphatic hydrocarbon radical having a number of carbon atoms in the specified range. Thus, for example, "$C_{2-6}$ alkyl" (or "$C_2$-$C_6$ alkyl") refers to any of the hexyl alkyl and pentyl alkyl isomers as well as n-, iso-, sec- and tert- or t-butyl, n- and isopropyl, and ethyl. As another example, "$C_{1-4}$ alkyl" refers to n-, iso-, sec- and t-butyl, n- and isopropyl, ethyl, and methyl.

The term "Aryl" refers to either phenyl, substituted phenyl, naphthyl, or substituted naphthyl, provided that substituted phenyl and substituted naphthyl each have 1 to 5 independently selected substitutents. Aryl substituents are illustrated in the first aspect above.

The term "cycloalkyl" refers to any monocyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The atoms in a compound described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds describe herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the Schemes and Examples herein using appropriate isotopically-enriched reagents and/or intermediates.

II. Herterocycle Synthesis

Scheme A illustrates the production of allyl-isoindoline (Compound 5), and different compounds that can be used to produce Compound 5.

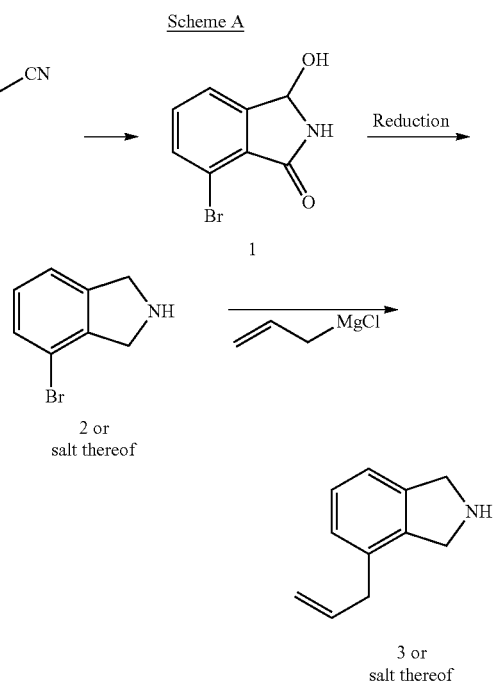

In a first aspect directed to heterocyclic formation, Compound 3 or salt thereof is produced by a method comprising the step of:

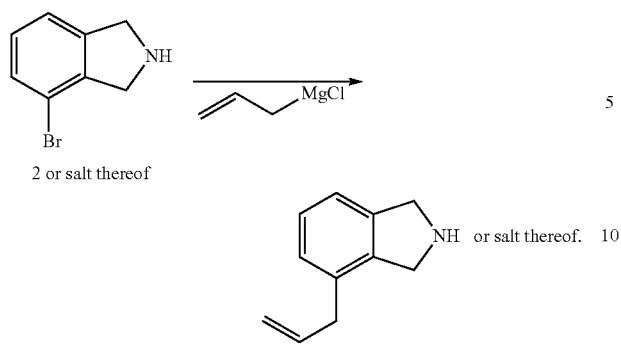

2 or salt thereof

3

Suitable reaction conditions include cross-coupling of Compound 2 with allyl magnesium chloride under Pd-catalyzed conditions. The reaction is also illustrated in Michael J. Zacuto et al., "*Preparation of 4-Allylisoindoline via a Kumada Coupling with Allylmagnesium Chloride,*" 15(1) Organic Process Research 158 (2011, published on line Dec. 6, 2010). (Not admitted to be prior art to the claimed invention.)

In a first embodiment, Compound 2 or salt thereof is made by a method comprising:

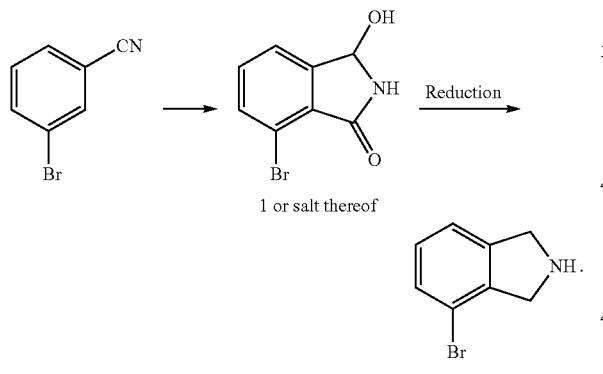

1 or salt thereof 2 or salt thereof

The first reaction is carried using a base and alkylformate. Examples of different bases include lithium diisopropyl amide (LDA); and lithium, sodium, or potassium hexamethyldisilazane. Suitable solvents include ether solvents such as diethylether, tetrahydrofuran (THF), methyl-THF, methyl-t-butyl ether (MTBE), diglyme, and dimethoxyethane. A general temperature range is −20° C. to −78° C.

Suitable reaction conditions for subsequent reduction of Compound 1 to provide Compound 2 include using sodium borohydride in the presence of $BF_3$ or etherate. Suitable solvents are aprotic organic. Examples of aprotic solvents include such as toluene, xylenes, chlorobenzene, and dichlorobenzene. A general temperature range from about 100° C. to about 130° C.

In another embodiment, Compound 2 or salt thereof is:

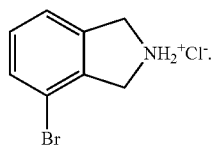

III. Side Chain Synthesis

Schemes B, C, and D illustrate the production of different compounds. Each of the steps provided in these schemes represent different embodiments. Further embodiments are provided by any combination of upstream and/or downstream steps.

Scheme B

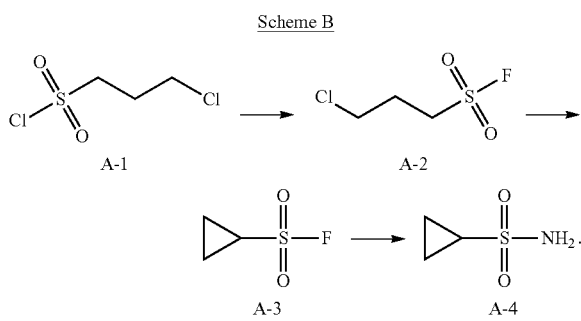

In an aspect concerning Scheme B, Compound A-3 is produced by a method comprising the steps of

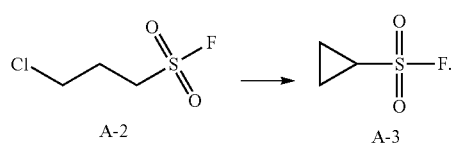

Suitable reaction conditions include heating A-2 in the presence of inorganic bases such as $K_2CO_3$, $Cs_2CO_3$, CO, and $K_3PO_4$ in aprotic solvents such as N,N-dimethylfomamide (DMF), dimethylacetamide (DMAc), N-methylpyrrolidone (NMP), or dimethylsulfoxide (DMSO) at 60° C. to 100° C.:

Scheme C

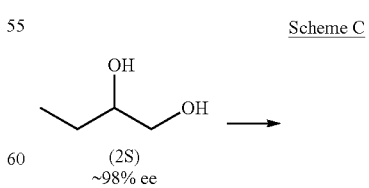

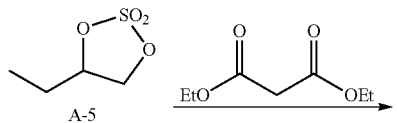

-continued

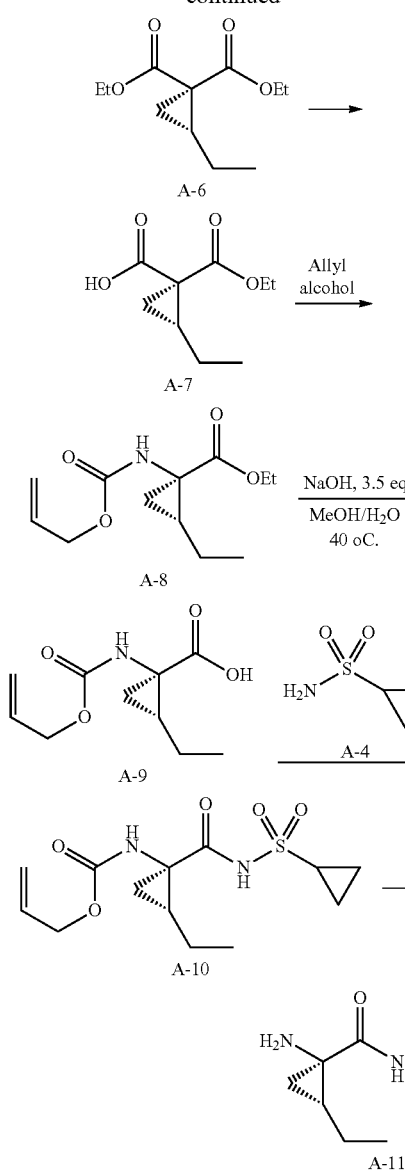

Different aspects and embodiments of Scheme C are directed to each of the different steps, alone or in any combination with up stream or downstream steps. For example, an embodiment is directed to:

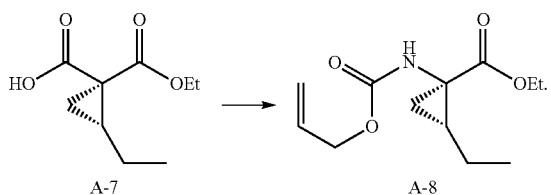

Suitable conditions include the use or allyl or benzyl alcohol, and a catalytic amount of Ti(OtBu)₄. Suitable solvents include aprotic solvents such as toluene, benzene, and xylenes, and chlorobenzene. A general temperature is from 65° C. to 100° C.

Another embodiment is:

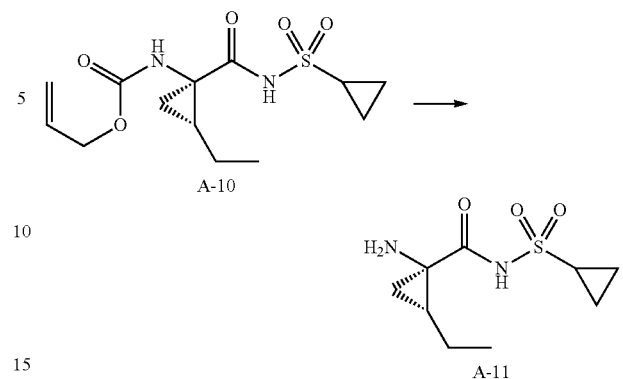

Suitable reaction conditions include the use of alcoholic solvents such as methanol, ethanol, propanol and butanol. A general temperature range is 20° C. to 50° C.

An embodiment that includes additional steps is:

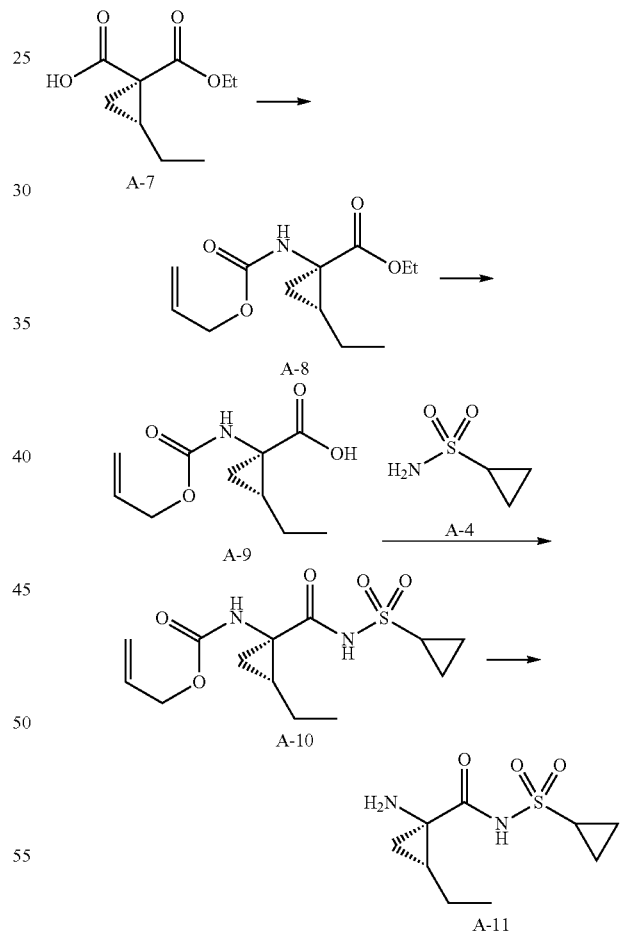

Examples of suitable conditions for the additional steps are provided in the Examples infra.

Additional aspects are directed to Compounds A-8, A-9, and A-10 or salts thereof; and substantially stereochemically pure A-6, A-7, A-8, A-9, or A-10 or salts thereof. Substantially stereochemically pure means that the indicated stereoisomer is present to a greater extent than other stereoisomers. In different embodiments, the indicated stereoisomer makes up at least 80%, at least 85%, at least 90%, at least 95% or at least 99% excess over other stereoisomers that could be present.

An alternative Scheme is provided by Scheme D:

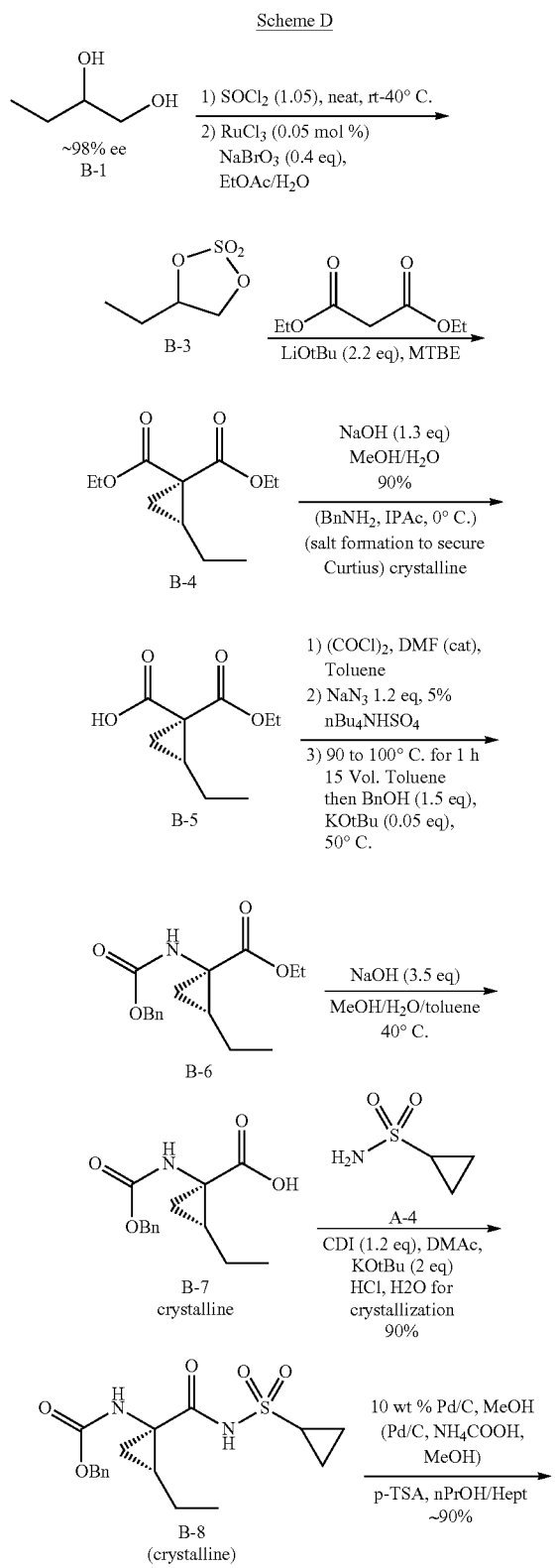

Different aspects and embodiments for Scheme D are directed to each of the different steps, alone or in any combination with up stream or downstream steps. Additional aspects include Compound B5 as a benzoamine salt, and Compounds B6, B7, and B8 and salts thereof.

IV. Macrolactam Production

Methods for marcolactam formation, producing intermediates for marcolactam formation, and side chain addition are illustrated in Scheme E. Scheme E illustrates macrolactam production using preferred groups. Alternative macrolactams using, for example, Formula I, II or III compounds can be produced based on the guidance provided herein.

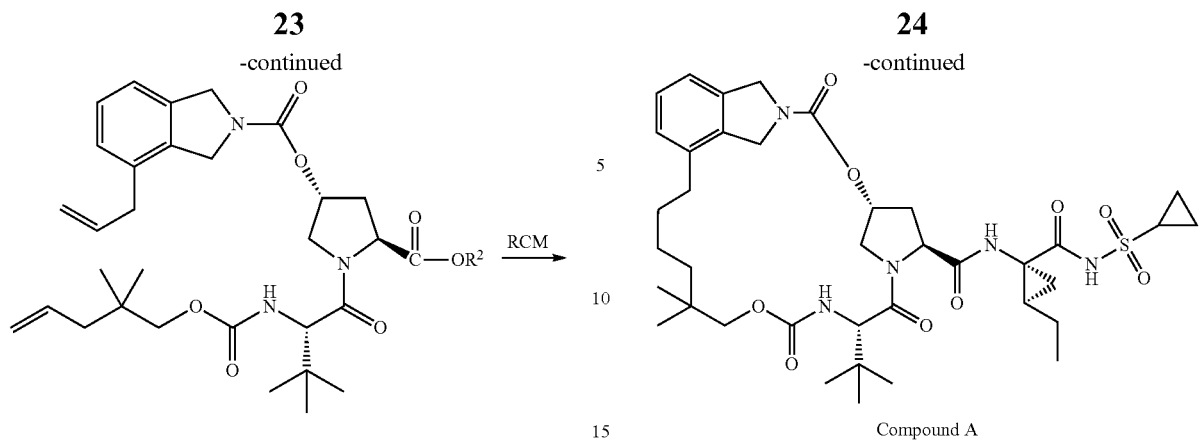

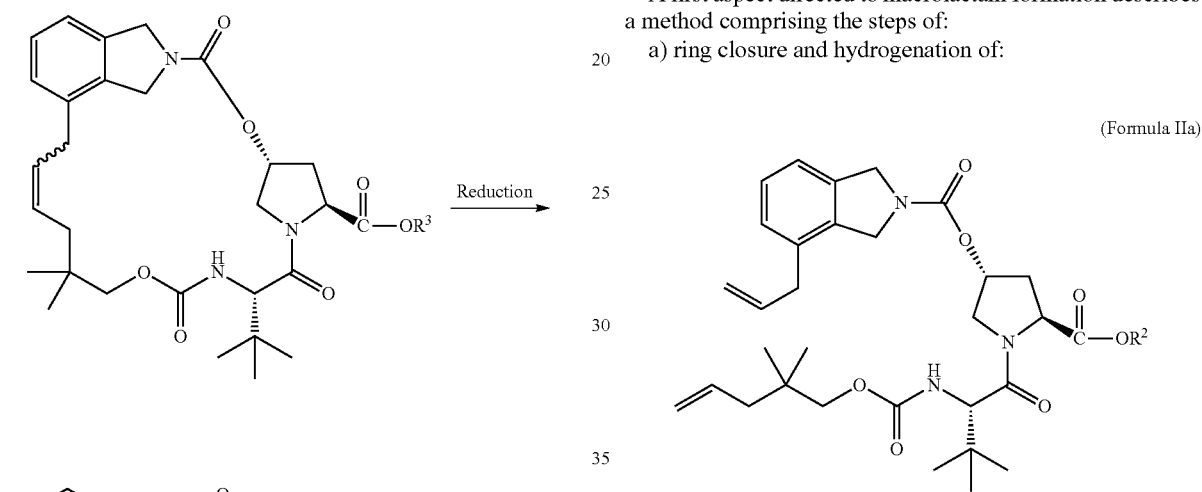

A first aspect directed to macrolactam formation describes a method comprising the steps of:
a) ring closure and hydrogenation of:

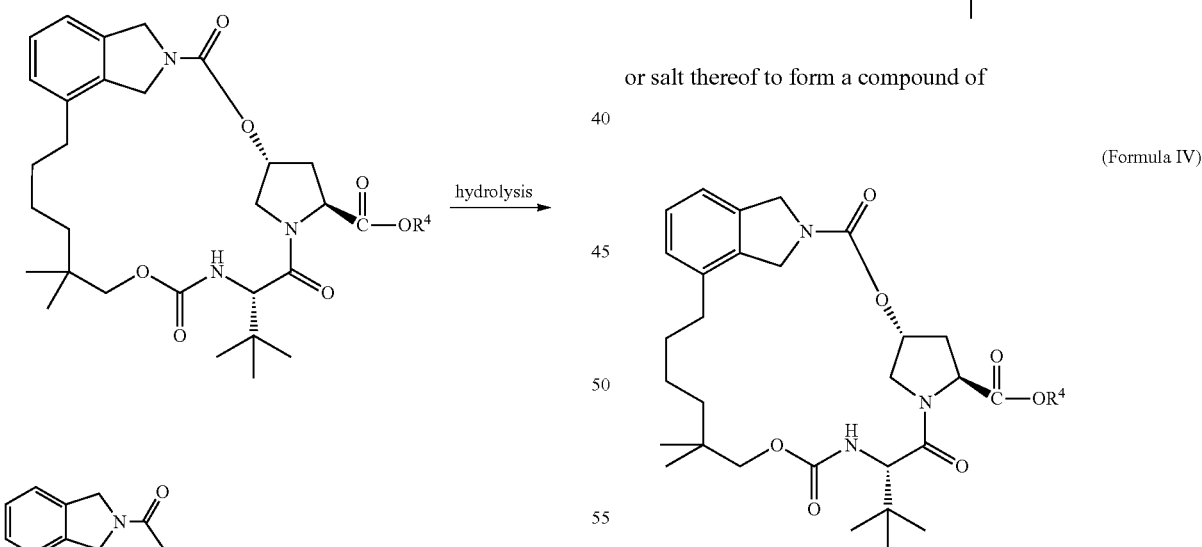

(Formula IIa)

or salt thereof to form a compound of (Formula IV)

or salt thereof;
wherein $R^2$ is as defined in the first aspect of section I. Intermediates supra., and $R^4$ is either H, $C_{1-6}$ alkyl, $C_3$-$C_8$ cycloalkyl, or Aryl.

A second aspect is directed to method of making Compound A comprising the steps of:
a) ring closure and hydrogenation of Formula IIa or salt thereof to form a compound of Formula IV or salt thereof and further comprising:

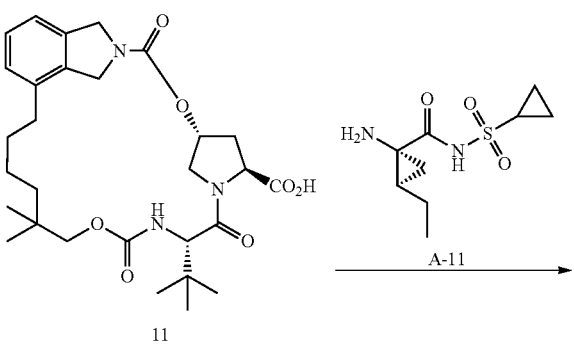

b) hydrolyzing the compound of Formula IV or salt thereof to form

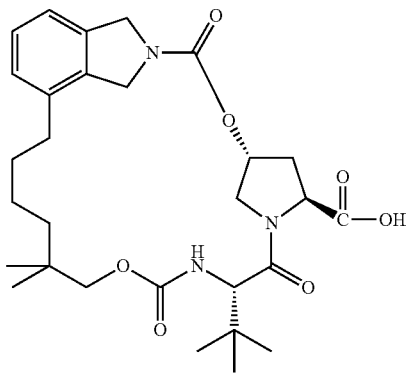

Compound 1 or salt thereof;

c) coupling Compound 1 or salt thereof to

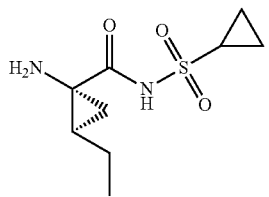

(A-11)

or salt thereof, to form Compound A or salt thereof, and d) optionally converting compound A or salt thereof into a pharmaceutically acceptable salt.

Suitable conditions for ring closure include aprotic solvents, such as IPAc, toluene, xylenes, mesitylene, and benzene. A general temperature range is 80° C. to 120° C.

Suitable conditions for hydrolyzing include using a caustic base at a temperature range of 0° C. to 50° C. (preferably room temperature), in an alcoholic solvent. Examples of suitable bases include lithium hydroxide, potassium hydroxide, and sodium hydroxide. Suitable alcoholic solvents include methanol, ethanol, propanol, and butanol.

Suitable conditions for coupling Compound A-11 include using a coupling reagent, an aprotic organic solvent and pyridine or pyridine derivatives. A general temperature is 0° C. to 50° C. (preferably room temperature). Examples of coupling reagents include dicyclohexylcarbodiimide (DCC), N,N-diisopropylcarbodiimide (DIC), 1-ethyl-3-(3-dimethylaminopropyl)carbodiimide hydrogen chloride (EDC-HCl) and 1-ethyl-3-(3-dimethylaminopropyl)carbodiimide (EDC). Examples of aprotic organic solvents include acetonitrile, THF, IPAc and toluene. In an embodiment, EDC is used.

The use of pyridine or a pyridine derivative instead of HOBt for coupling offers several advantages including higher yield and less epimerization on the proline α-center. In addition, HOBt is shock sensitive in a dry state.

Preferred pyridine derivatives have electron donating or neutral R groups at the 3 and 4 positions. Examples of general structures covering pyridine and derivatives include:

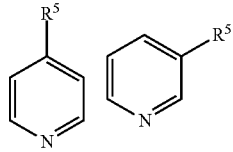

wherein $R^5$ is either hydrogen, Aryl, halogen, $C_{1-6}$ alkyl, O—$C_{1-6}$ alkyl or $C_3$-$C_8$ cycloalkyl. Preferred reagents are pyridine and 4-phenylpyridine, 4-alkylpyridine, methylpyridine, 3- or 4-mono or dialkylpyridine, wherein the alkyl group can be a $C_{1-6}$ alkyl.

A third aspect is directed to producing Compound A comprising the steps of coupling Compound 1 with Compound A-11 using pyridine or a pyridine derivative. Preferably, no detectable HOBt is present.

Additional embodiments include:

In a first embodiment, $R^2$ of the Formula IIa compound is either H, $C_{1-6}$ alkyl, $C_3$-$C_8$ cycloalkyl, phenyl or naphthyl.

In a second embodiment, $R^2$ of the Formula IIa compound is either H, $C_{1-6}$ alkyl or $C_3$-$C_8$ cycloalkyl.

In a third embodiment, $R^2$ of the Formula IIa compound is $C_{1-6}$ alkyl.

In a fourth embodiment, the compound is a salt of Formula IIa. In a further embodiment, the salt is either potassium, sodium, lithium, a primary amine ($NH_3^+$—$R^C$), a secondary amine ($NH_2^+$—$(R^C)_2$), or a tertiary amine ($NH^+$—$(R^C)_3$), wherein each $R^C$ is independently $C_{1-6}$ alkyl, $C_3$-$C_8$ cycloalkyl, or Aryl; provided that two $R^C$ can together form a three to eight membered heterocyclic group containing N and —$(CH_2)_n$—, where n is 2-7, preferably 5 or 6.

In a fifth embodiment, the Formula IIa compound or salt thereof is Compound 8.

In a sixth embodiment, the Formula IIa compound or salt thereof is Compound 8B.

In a seventh embodiment, the Formula II compound or salt thereof is Compound 8C.

In an eighth embodiment, $R^4$ of the Formula IV compound is either H, $C_{1-6}$ alkyl, $C_3$-$C_8$ cycloalkyl, phenyl or naphthyl, and $R^2$ is as provided in the first aspect or any of embodiments 1-8.

In a ninth embodiment, $R^4$ of the Formula IV compound is $C_{1-6}$ alkyl, and the compound of Formula IIa or salt thereof is as provided in the first aspect or second aspect, or any of embodiments 1-8.

In a tenth embodiment, a compound of Formula IV or salt thereof is:

(Compound 11)

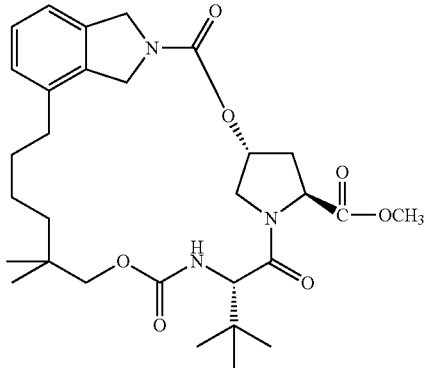

or salt thereof and the compound of Formula IIa or salt thereof is as provided in the first aspect or second aspect, or any of embodiments 1-8.

$R^2$ and $R^4$ are preferably the same for a particular ring closing and hydrogenation reaction. But $R^2$ and $R^4$ can be different, for example, if the $R^2$ group is modified after ring closure and prior to reduction.

In an eleventh embodiment, the method further comprising the step of producing the compound of Formula IIa or salt thereof comprising the step of coupling Formula Ia

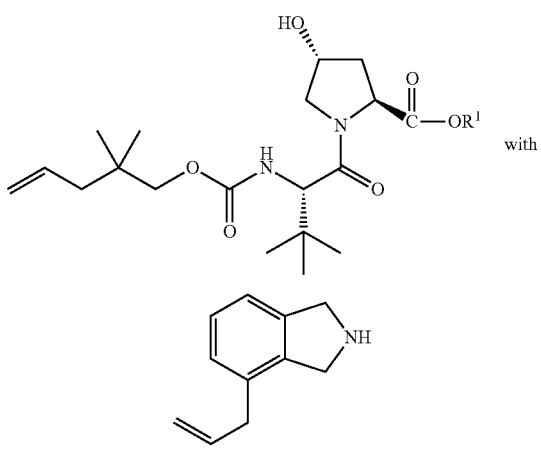

or a salt thereof, wherein $R^1$ is as defined in section I. Intermediates supra. I.

In a twelfth embodiment, the method further comprises the step of making the compound of Formula I by coupling (Compound 6A)

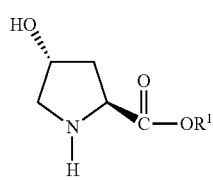

or salt thereof and

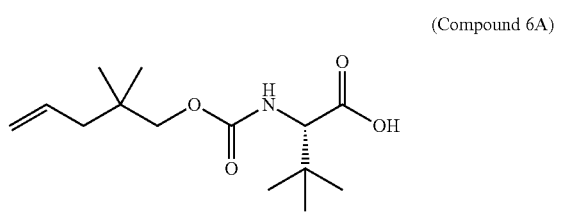 [SMILES: C=CCC(C)(C)COC(=O)N[C@H](C(=O)O)C(C)(C)C]

or salt thereof; wherein $R^1$ is as defined in section I. Intermediates supra.

In a thirteenth embodiment, $R^1$ for the eleventh or twelfth embodiments is either H, $C_{1-6}$ alkyl, or $C_3$-$C_8$ cycloalkyl. In a further embodiment, $R^1$ is methyl.

In a fourteenth embodiment, Compound 6A or salt thereof is

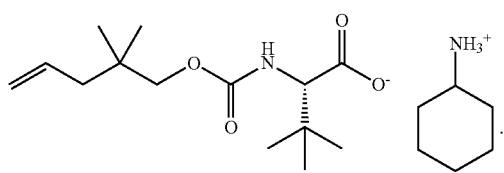 [SMILES: C=CCC(C)(C)COC(=O)N[C@H](C(=O)[O-])C(C)(C)C ; [NH3+]C1CCCCC1]

In a fifteenth embodiment,

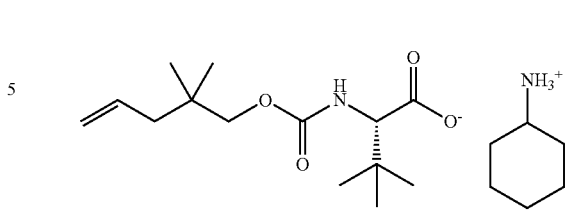

is made by a process comprising the following steps:

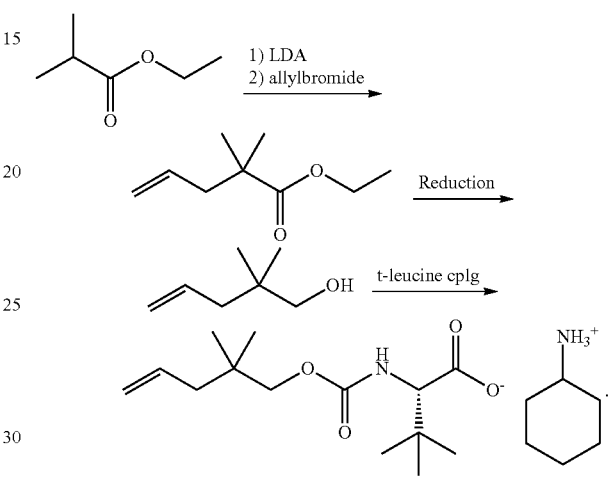

In a sixteenth embodiment, the ring closure is performed by simultaneous slow addition of catalyst and the compound of Formula IIa to a solvent at approximately the same time, wherein:

the solvent is provided at about 5-25 liters per Kg of substrate, preferably about 10 L per Kg of substrate;

the catalyst is provided at a concentration of about 250 ml to 3 L per Kg of catalyst, preferably about 1 L per Kg of catalyst;

the compound is provided at a concentration of about 500 ml to 6 L per Kg of substrate, preferably about 2 L per Kg of substrate; and the compound-solution, the catalyst-solution and the solvent are combined together over a period of 0.5-2.5 hrs, preferably over about 1.25 hours.

The reaction can be carried out using different solvents, catalysts, and temperature ranges. A general temperature range is 50° C. to 150° C. Different type of organic and inorganic solvents can be employed. Examples of solvents include toluene, benzene, acetonitrile, dichloroethane, dichloromethane, isopropylacetate, ethylacetate, and alcohols (e.g., isopropanol, methanol, and ethanol). Examples of suitable catalysts include N-hetereocyclic carbene ruthenium-alkylidenes, phosphone ruthenium-alkylidenes molybdenum-alkylidenes, ruthenium-carbene, and molybdenum-carbene. A preferred set of conditions is using toluene, at a temperature range of 80° C. to 110° C., and the catalyst Grubbs-Hoveyda II.

V. Salts

Compounds described herein having appropriate functional groups can be provided as salts. Pharmaceutically acceptable salts can be used with compounds for treating patients. Non-pharmaceutical salts may, however, be useful in the preparation of intermediate compounds.

Pharmaceutically acceptable salts are suitable for administration to a patient, preferably, a human. Suitable salts include acid addition salts which may, for example, be formed by mixing a solution of a compound with a solution of a pharmaceutically acceptable acid such as hydrochloric acid, sulfuric acid, acetic acid, trifluoroacetic acid, or benzoic acid. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

VI. Administration and Compostitions

Compounds having therapeutic applications, such as Compound A, can be administered to a patient infected with HCV. The term "administration" and variants thereof (e.g., "administering" a compound) means providing the compound or a prodrug of the compound to the individual in need of treatment. When a compound is provided in combination with one or more other active agents (e.g., antiviral agents useful for treating HCV infection), "administration" and its variants are each understood to include concurrent and sequential provision of the compound or salt and other agents.

As used herein, the term "prodrug" is intended to encompass an inactive drug form or compound that is converted into an active drug form or compound by the action of enzymes, chemicals or metabolic processes in the body of an individual to whom it is administered.

As used herein, the term "composition" is intended to encompass a product comprising the specified ingredients, as well as any product which results, directly or indirectly, from combining the specified ingredients.

By "pharmaceutically acceptable" is meant suitable for administration to a subject.

The term "subject" (alternatively referred to herein as "patient") as used herein refers to an animal, preferably a mammal, most preferably a human, who has been the object of treatment, observation or experiment.

The term "effective amount" indicates a sufficient amount to exert a therapeutic or prophylactic effect. For a patient infected with HCV, an effective amount is sufficient to achieve one or more of the following effects: reduce the ability of HCV to replicate, reduce HCV load, and increase viral clearance. For a patient not infected with HCV, an effective amount is sufficient to achieve one or more of the following: a reduced susceptibility to HCV infection, and a reduced ability of the infecting virus to establish persistent infection for chronic disease.

For the purpose of inhibiting HCV NS3 protease and treating HCV infection and/or reducing the likelihood or severity of symptoms of HCV infection, the compounds, optionally in the form of a salt, can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice.

Compounds can, for example, be administered by one or more of the following routes: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further guidance for methods suitable for use in preparing pharmaceutical compositions is provided in *Remington's Pharmaceutical Sciences*, 20$^{th}$ edition (ed. A. R. Gennaro, Mack Publishing Co., 2000).

Therapeutic compounds can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, 500, and 750 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

VII. HCV Inhibiroty Activity

The ability of a compound to inhibit HCV NS3 activity, HCV replicon activity, and HCV replication activity can be evaluated using techniques well-known in the art. (See, for example, Carroll et al., *J. Biol. Chem.* 278:11979-11984, 2003.) One such assay is a HCV NS3 protease time-resolved fluorescence (TRF) assay as described below and in Mao et al., *Anal. Biochem.* 373:1-8, 2008 and Mao et al., WO2006/102087.

VIII. EXAMPLES

The examples provided below are intended to illustrate the invention and its practice. Unless otherwise provided in the claims, the examples are not to be construed as limitations on the scope or spirit of the invention.

Abbreviations used herein include the following:
MTBE=methyl-tert-butyl ether
CPME=cyclopentyl methyl ether
DMAC=Dimethylacetamide DCM=dichloromethane
DMF=dimethylformamide
THF=tetrahydrofuran
DPPM=diphenylphosphinomethane
DPPE=diphenylphosphinoethane
DPPP=diphenylphosphinopropane
LDA=lithium diisopropylamide
PhMe=toluene
IPA=isopropyl alcohol
IPAc=isopropyl acetate
RB=round bottom
TEA=triethylamine
CDI=1,1'-carbonyldiimidazole
EDC-HCl=1-Ethyl-3-(3-dimethylaminopropyl)carbodiimide hydrochloride
DI=deionized
GH-II=Grubbs-Hoveyda 2nd generation catalyst—(1,3-Bis-(2,4,6-trimethylphenyl)-2-imidazolidinylidene)dichloro(o-isopropoxyphenylmethylene)ruthenium)
DIPEA=hunig's base=diisopropylethylamine Example 1

Side Chain Synthesis

Compound A11 was produced using the methods described in this example. The compounds and methods described in the example provide for different aspects and embodiments of the present invention.

1. Activation

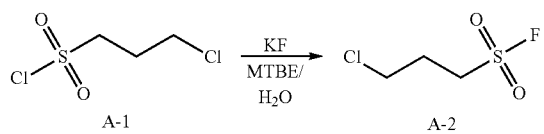

To a mixture of potassium fluoride (3.28 g, 56.5 mmol) in methyl-tert-butyl ether (MTBE) (25.00 ml) and water (15.00 ml) was added 3-chloropropanesulfonyl chloride (5.0 g, 28.2 mmol). The mixture was stirred at ambient temperature for 12 hours. The MTBE layer was separated and washed with water (25.00 ml) and concentrated to a liquid: 3-chloropropanesulfonyl fluoride (A-2, 4.54 g, 28.2 mmol, 98% yield).

2. Cyclization and Amidation

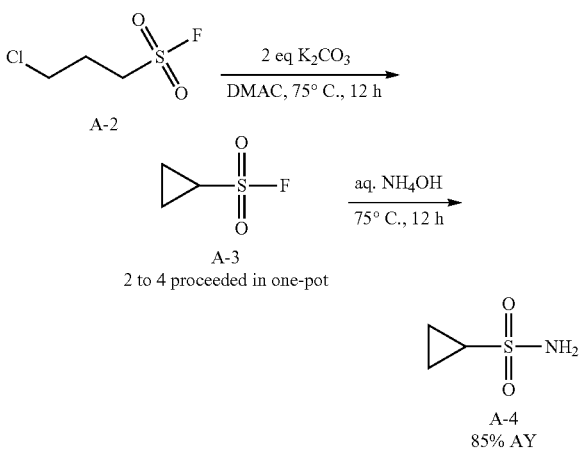

A mixture of chloropropanesulfonyl fluoride (3.2 g, 19.93 mmol) and $K_2CO_3$ (5.5 g, 40 mmol) in dimethyl acetamide (DMAc, 16.00 ml) was heated at 65° C. to 75° C. for 12 hours to complete the reaction. The mixture was cooled to room temperature, filtered and inorganics cake was washed with DMAc (8 mL). The filtrate and wash were combined, followed by addition of aq. ammonia (11.31 g, 199 mmol). The mixture was heated at 65° C. to 75° C. in a sealed vessel for another 12 hours to afford cyclopropyl sulfonyl amide A-4 (85% assayed yield).

3. Dial Protection

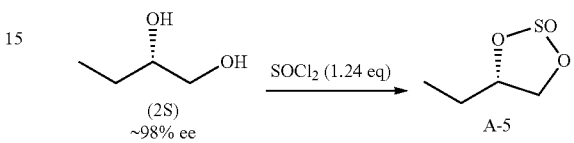

Procedure A:

To an ice-cooled solution of (S)-1,2-butanediol (100 mg, 1.1 mmol) in dichloromethane (DCM) (0.3 mL) was charged thionyl chloride (0.1 mL, 1.35 mmol) in DCM (0.2 mL), then the ice bath was removed and reaction was aged at ambient temperature for 2 hours to reach completion by $^1$H NMR monitoring. The reaction was quenched by water with cold bath to keep temperature <25° C. The organic layer was washed with water twice and was directly used in the next step.

Procedure B:

To ice-cooled neat (S)-1,2-butanediol (10.0 g, 110 mmol) was charged thionyl chloride (8.42 mL, 115 mmol) slowly with cold bath, the first half addition is exothermic, kept T<40° C. with cold bath and addition rate, the second half of addition is endothermic, removed cold bath, put warm bath, kept T 10° C. to 20° C., during the addition a lot of HCl gas was formed, well ventilate and scavenge to 2N NaOH solution. Aged at room temperature for 30 minutes. Reaction went to completion monitored by NMR or GC (2:3 dr ratio). The reaction was diluted with EtOAc (80 mL), quenched with water (80 mL) with cold bath, kept T ~20° C. to 25° C. Cut the aqueous layer, washed organic layer with water (100 mL) once (the last aqueous layer pH ~1-2).

4. Oxidation

Procedure A:

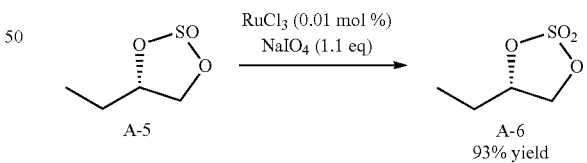

To an ice-cooled soln of Compound A-5 (0.5 g, 3.6 mmol) in MeCN (1.5 mL) and DCM (1.5 mL) was added water (3 mL), Ruthenium (III) trichloride (0.075 mg, 0.0036 mmol) followed by sodium periodate (0.85 g, 3.96 mmol). The ice bath was removed and reaction mixture turned to slurry and reached completion after 2.5 hours at ambient temperature. Reaction was monitored by NMR or GC. Reaction slurry was filtered through SOLKA-FLOC to remove precipitate, rinsed with 10 vol MTBE. The organic layer was washed with brine (2×3 mL) to give 0.53 g product A-6 (97.4% assayed yield by NMR).

Procedure B:

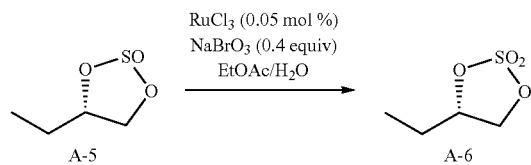

To above organic solution of compound A-5 (110 mmol) in 80 mL EtOAc was charged water (80 mL), charged RuCl₃·H₂O (11 mg, 0.055 mmol). The mixture was stirred for ~10 mins until it was all dissolved and NaBrO₃ (6.63 g, 44 mmol) was added portion-wise in ~40 mins (Temp. increase delay ~10 mins), kept T<40° C. After addition, aged at 30° C. for ~1-2 hours to reach completion as monitored by NMR or GC. The organic layer was separated and the aqueous layer was removed and back extracted once with EtOAc (30 mL). The organic layer were combined and washed with 5 wt % aq. NaHSO₃ (60 mL) and brine (60 mL). The organic layer was concentrated and used in next step as a MTBE solution. Typical NMR or GC overall assay yield: 85-89%.

5. Alkylation

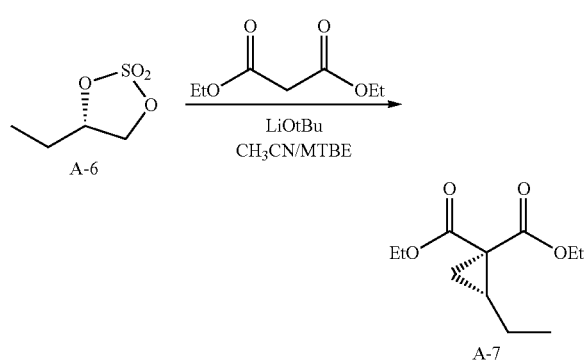

To a slurry of LiOtBu (5.3 g, 66.2 mmol) in 30 ml acetonitrile (under N₂/mechanical stirring/water bath) was slowly charged a solution of Compound A-6 and diethyl manolate (5.05 g, 31.5 mmol) in 10 mL acetonitrile via additional funnel over 30 min (reaction temperature controlled below 30° C.). The reaction was stirred at ambient temperature for 1 hour and at 40° C. for 2 hour. The reaction gave ~95% conversion as monitored by GC.

The reaction mixture was quenched with 40 mL water, extracted with 40 mL MTBE and the aqueous layer was back extracted once with 20 mL MTBE. The combined organic layers were concentrated to give Compound A-7 as clear oil (NMR assay ~89% yield).

Achiral GC conditions: Restek RTX-1 (15 m×320×1 um) isotheromal 130° C. detector and inlet heater set at 250° C., 100:1 split ratio, constant pressure mode set at 9 psi (flow velocity~54 cm/sec) total runtime is 5 minutes.

| Compound | RT (minutes) U |
|---|---|
| Malonate ester | 1.54 |
| Compound A-6 | 2.10 |
| Compound A-7 | 4.57 |

6. Hydrolysis

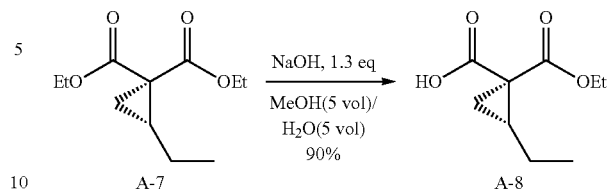

To an ice cold solution of Compound A-7 (52 g, 81% wt, 198 mmol) in 150 mL MeOH was charged a soln of NaOH (10.75 g, 262 mmol) in water (150 mL) via additional funnel over 20 min (the reaction temperature was controlled below 20° C.). The reaction slurry was gradually warmed to and stirred at room temperature overnight. The reaction was cooled with ice bath to 13° C. Water (250 mL) was charged followed by ethyl acetate (250 mL). The aq. layer was extracted with ethyl acetate (100 mL), and aq layer was acidified with conc. HCl (25 mL) to pH 2.1. The resulting aq. layer was extracted with ethyl acetate (2×200 mL). The combined organic layers were washed with brine (2×100 mL), concentrated under vacuum to give Compound A-8 as a clear oil (35.6 g, 94 wt %, 90% yield).

HPLC method: Ascentis R Express C18, 10 cm×4.6 mm, 2.7µ; standard gradient: 10-95% of B in 6 minutes (A=0.1% phosphoric acid, B=acetonitrile), 2 min hold, 2 min post; Flow rate: 1.8 ml/min; UV detection at 210 nm, 40° C.

| Compound | RT (minutes) |
|---|---|
| Compound A-7 | 4.76 mins |
| Compound A-8 | 3.29 mins |

7. Curtius Arrangement

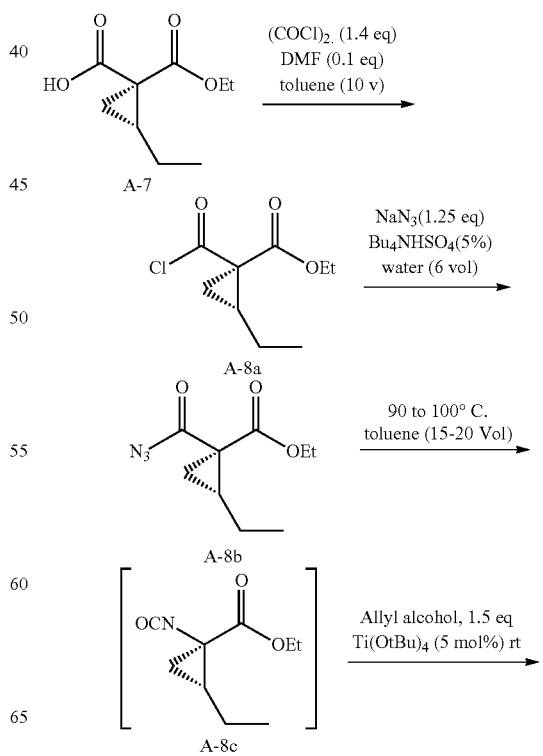

8. Hydrolysis

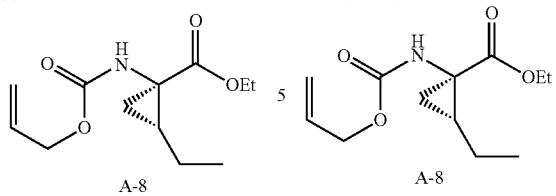

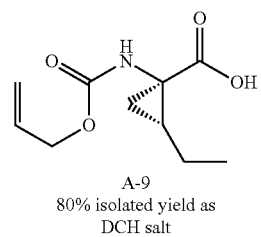

Preparation of acid chloride A-8a: Compound A-7 (2.0 g, 10 mmol) was dissolved in 20 ml of toluene, cooled with ice bath to 5° C., added DMF (0.079 g, 0.083 mmol), then added (COCl)$_2$ (1.91 g, 15 mL) slowly and kept the reaction temperature <20° C. After addition, the reaction was aged at ambient temperature for ~30 to 60 min or until GC assay showed full conversion. The reaction was cooled with ice bath and quenched with water (20 mL). The org. layer was washed with 10 wt % NaHCO$_3$ twice (2×10 mL) to pH ~8.0. The acid chloride solution with toluene was directly taken to the next step.

Preparation of acyl azide A-8b: To water (12 mL) in a flask was added sodium azide and tetrabutylammonium hydrogen sulfate (0.18 g, 0.535 mmol). The solution of acid chloride (A-8a) in toluene was added to this sodium azide solution over 30-60 min with vigorous stirring (>400 RPM). The mixture was stirred at ambient temperature for ~1-2 hours until GC assay showed full conversion. The organic layer was separated, washed sequentially with 1M NaHCO$_3$ (60 mL), water (50 mL) and brine to give a solution with water content at KF ~700 ppm. The solution was further dried over MgSO$_4$, and filtered to give an acyl azide solution (KF ~100 ppm) in toluene which was directly taken to next step.

Preparation of Compound A-8: A 3-necked flask (500 mL) connected with additional funnel and condenser was vacuumed/flushed with N$_2$ 3 times. Toluene (10 mL, KF under 50 ppm) was charged and heated to 95° C. (internal temperature). To the heated toluene was charged the acyl azide solution over 60 min and the temperature was maintained at 90° C. to 100° C. After addition, the reaction solution was aged for ~1 hour at this temperature. The reaction was cooled to ~20° C., allyl alcohol (0.94 g, 16.11 mmol) was added followed by the addition of Ti(OtBu)$_4$ (0.18 g, 0.54 mmol), the reaction was stirred at ambient temperature until GC assay showed full conversion. The reaction was quenched with 1 N HCl (44 mL). The organic layer was washed with water and brine, and concentrated to give Compound A-8 as a pale yellow liquid.

HPLC conditions: Aglient Eclipse plus C18, 4.6×50 mm, 1.8µ; RT, linear gradient: 10-90% of B(MeCN) in 5 minutes, hold to 2 min; A: 0.1% H$_3$PO$_4$ of water solution; Flow rate: 1.0 ml/min; UV detection at 210 nm.

| Compound | RT (min) |
|---|---|
| Toluene | 4.85 |
| Acyl azide intermediate A-8b | 4.93 |
| Isocyanate intermediate A-8c | 5.31 |
| Compound A-8 | 4.43 |

To a solution of Compound A-8 in toluene (7.79 g, 32.3 mmol, 14 mL, ~2 volume) was charged a solution of NaOH (3.95 g, 96.9 mmol) in water (10 mL) at ambient temperature (internal temperature raised to 28° C.). The resulting solution was heated at 40° C. for 4 hours (90% conversion), then stirred at ambient temperature overnight (95% conversion).

The reaction was cooled to 6° C. with ice bath; water (70 mL) and toluene (34 mL) were charged (temperature raised to 15° C.). The aq. layer was extracted with IPAc (30 mL). The remaining aq. layer was cooled with ice bath and acidified with 5N HCl (35 mL) to pH 2.1 and extracted with ethyl acetate twice (1×50 mL, 1×30 mL). The combined organic layers were washed with water 30 mL and brine 30 mL (pH 1.9), dried over MgSO$_4$, filtered and concentrated to give Compound A-9 as clear liquid. (5.93 g, 86% assayed yield from compound A-8 by NMR).

HPLC method: Ascentis R Express C18, 10 cm×4.6 mm, 2.7µ; standard gradient: 10-95% of B in 6 minutes (A=0.1% phosphoric acid, B=acetonitrile), 2 min hold, 2 min post; Flow rate: 1.8 ml/min; UV detection at 210 nm, 40° C.

| Compound | RT (min) |
|---|---|
| Compound A-8 | 4.0 |
| Compound A-9 | 2.89 |

9. CDI Coupling

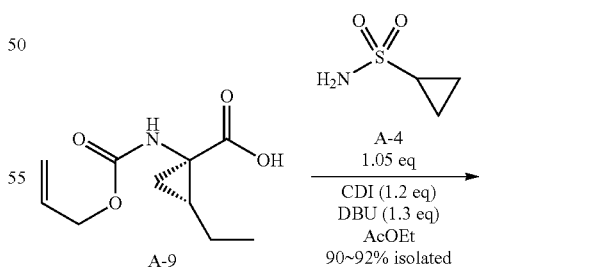

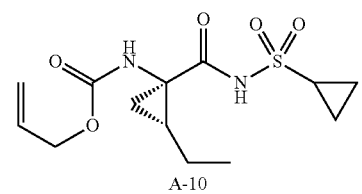

To a solution of Compound A-9 (3.24 g, 97 W %, 14.74 mmol) in anhydrous ethyl acetate (33 mL) was charged CDI (2.92 g, 17.69 mmol, 1.1 eq) under $N_2$. Three minutes later, the reaction was heated to 40° C. for 1 hour. Another 0.1 eq CDI was charged and the mixture was heated for another 1 hour to reach completion. The reaction was cooled to 12° C. in an ice bath. DBU (2.98 g, 19.16 mmol) was charged followed by cyclopropyl sulfonamide A-4 (1.88 g, 15.48 mmol). The reaction mixture was heated at 40° C. for 1 hour, cooled to 3° C. in an ice bath, and quenched with 3 N HCl (20 mL) to pH 2.5. Compound A-10 partially precipitated out. The precipitate was collected by filtration, rinsed with water. The organic layer after filtration was washed with water (15 mL) and brine (15 mL). The organic layer and the precipitate were combined, concentrated under vacuum to give Compound A-10 as white powder (~4.2 g, 90-92% yield).

HPLC conditions: Aglient Eclipse plus C18, 4.6×50 mm, 1.8µ; RT, linear gradient: 10-90% of B(MeCN) in 5 minutes, hold to 2 min; A: 0.1% $H_3PO_4$ of water soln; Flow rate: 1.0 ml/min; UV detection at 210 nm.

| Compound | RT (min) |
|---|---|
| Compound A-9 | 3.36 |
| Compound A-10 | 4.8 |

10. Deprotection and Salt Formation

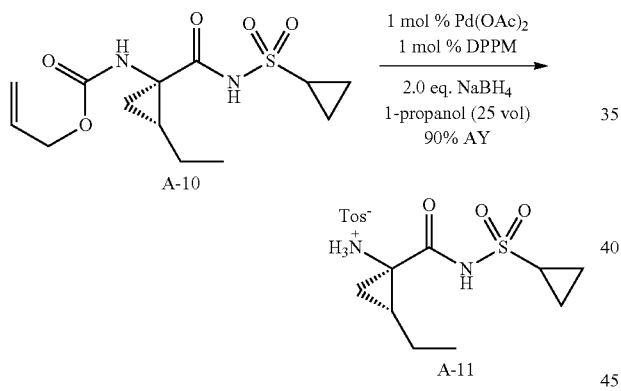

Catalyst activation: To $Pd(OAc)_2$ (6.4 mg, 0.028 mmol) was charged 2-Me-THF or THF (0.1 mL), DPPM (10.9 mg, 0.0284 mmol) followed by N-Methylcyclohexylamine (11 µl). The resulting slurry was aged at ambient temperature for 30 min. Then 10 µl of this solution was used for next solution.

Reaction procedure: To a 8 ml Vial was charged Compound A-10 (100 mg, 0.284 mmol) and 1-propanol (2.5 mL). This slurry was aged at 40° C. for 30 min, cooled. $NaBH_4$ (21.52 mg, 0.568 mmol) was added followed by addition of a solution of the activated catalyst (0.01 mL). The reaction mixture was stirred at ambient temperature for 5 min, warmed to 40° C. and aged at this temperature for 16.5 hour. (~90% assayed yield by NMR). The reaction was cooled, charged TsOH (57 mg, 0.3 mmol) 1 eq) and stirred at ambient temperature. Heptane was added to crystallize the product.

HPLC conditions: Aglient Eclipse XDB, 4.6×50 mm; RT, linear gradient: 5-95% of B(MeOH) in 5 minutes, hold to 8 min; A: pH 3.5 (10 ml of stock soln diluted to 1 L)+200 mM sodium perchlorate monohydrate (stock soln: 12.6 g ammonium formic formate+7.9 ml formic acid); Flow rate: 1.0 ml/min; UV detection at 210 nm.

| Compound | RT (min) |
|---|---|
| Compound A-10 | 4.8 |
| Compound A-11 | 2.74 |
| TsOH | 2.52 |

11. Curtius Arrangement

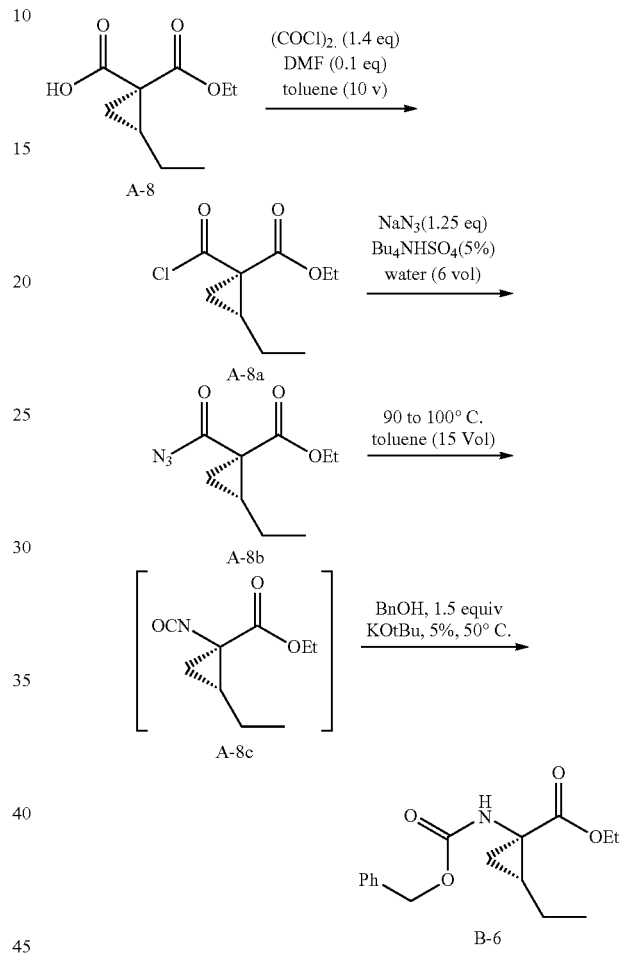

Preparation of acid chloride A-8a: Compound A-8 (2.0 g, 10 mmol) was dissolved in 20 ml of toluene, cooled with ice bath to 5° C., added DMF (0.079 g, 0.083 mmol), then added $(COCl)_2$ (1.91 g, 15 mL) slowly and kept the reaction temperature <20° C. After addition, the reaction was aged at ambient temperature for ~30 to 60 min or until GC assay showed full conversion. The reaction was cooled with ice bath and quenched with water (20 mL). The organic layer was washed with 10 wt % $NaHCO_3$ twice (2×10 mL) to pH ~8.0. The acid chloride solution with toluene was directly taken to the next step.

Preparation of acyl azide A-8b: To water (12 mL) in a flask was added sodium azide and tetrabutylammonium hydrogen sulfate (0.18 g, 0.535 mmol). The solution of acid chloride (A-8a) in toluene was added to this sodium azide solution over 30-60 min with vigorous stirring (>400 RPM). The mixture was stirred at ambient temperature for ~1-2 hours until GC assay showed full conversion. The organic layer was separated, washed sequentially with 1M $NaHCO_3$ (60 mL), water (50 mL) and brine to give a solution with water content at KF ~700 ppm. The solution was further dried over MgSO$_4$, and filtered to give an acyl azide solution (KF<100 ppm) in toluene which was directly taken to next step.

Preparation of compound B-6: A 3-necked flask (500 mL) connected with additional funnel and condenser was vacuumed/flushed with N$_2$ 3 times. Toluene (10 mL, KF under 50 ppm) was charged and heated to 95° C. (internal temperature). To the heated toluene was charged the acyl azide solution over 60 min and the temperature was maintained at 90° C. to 100° C. After addition, the reaction solution was aged for ~1 hour at this temperature. The reaction was cooled to ~20° C.

In another flask charged BnOH (15 mmol), KOtBu (0.5 mmol) and 6 ml toluene, added the above isocyanate toluene solution in 1 hour via additional funnel at 30° C., some exthermo, kept T<50° C., aged 2-4 hrs at 50° C. until it went to completion by HPLC or GC. The reaction was quenched with water (44 mL), and washed with water once. The assay yield of Compound B-6 is ~85%. Solvent switch of Compound B-6 toluene solution to MeOH and used in the next step.

HPLC conditions: Aglient Eclipse plus C18, 4.6×50 mm, 1.8μ; RT, linear gradient: 10-90% of B(MeCN) in 5 minutes, hold to 2 min; A: 0.1% H$_3$PO$_4$ of water solution; Flow rate: 1.0 ml/min; UV detection at 210 nm.

| Compound | RT (min) |
| --- | --- |
| Toluene | 4.85 |
| Acyl azide intermediate A-8b | 4.93 |
| Isocyanate intermediate A-8c | 5.31 |
| Compound B-6 | 4.43 |

12. Hydrolysis

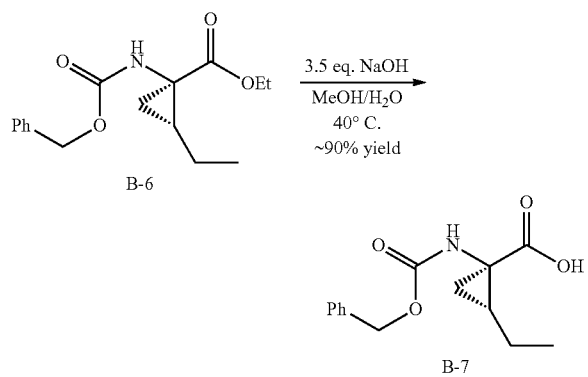

To a solution of Compound B-6 in MeOH (5v) was charged a solution of NaOH (10N, 3.5 equiv) in water (5v) at ambient temperature and temperature raised to ~28° C. The resulting solution was heated at 40° C. for 8-12 hours to give full conversion by HPLC.

The reaction was cooled to 6° C. with ice bath; water (20 mL), MTBE (10 mL) and heptane (20 mL) were charged, and cut off the organic layer to remove almost all BnOH from rearrangement step. The aq. layer was acidified with 12N HCl to pH 2.1 and extracted with IPAc twice. The combined organic layers were washed with water 30 mL and brine 30 mL (pH 1.9). Azotrop the organic phase and flushed with IPAc to KF<200 ppm. Kept IPAc 4 v and added heptane 8-10v at 40° C., cooled to room temperature and aged at 2° C. for 2 hour. The solid was collected by filtration and washed with heptane to give B-7 solid with 90-94% yield.

HPLC method: Ascentis R Express C18, 10 cm×4.6 mm, 2.7μ; standard gradient: 10-95% of B in 6 minutes (A=0.1% phosphoric acid, B=acetonitrile), 2 min hold, 2 min post; Flow rate: 1.8 ml/min; UV detection at 210 nm, 40° C.

| Compound | RT (min) |
| --- | --- |
| Compound B-6 | 5.43 |
| Compound B-7 | 4.69 |
| BnOH | 2.01 |

13. CDI Coupling

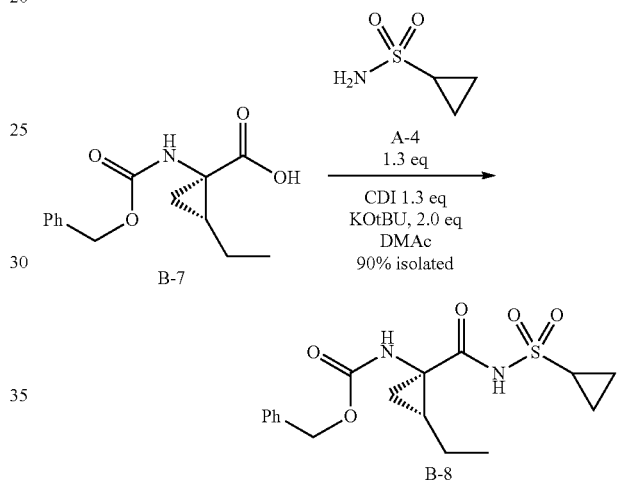

To a solution of Compound B-7 (1.0 g, 3.8 mmol) in dry DMAc (10 mL) was charged CDT (0.83 g, 5.1 mmol, 1.3 eq) under N$_2$. The reaction was heated to 40° C. for 30 min-1 hour until HPLC (quenched with nBuNH$_2$ in CH$_3$CN) shows completion. The reaction was cooled to 20° C. in an ice bath. KOtBu (0.85 g, 7.6 mmol) was charged followed by cyclopropyl sulfonamide A-4 (0.59 g, 4.9 mmol). The reaction mixture was heated at 40° C. until HPLC shows completion and cooled to room temperature and quenched with 2 N HCl (10 mL) to pH ~2. Added 20 ml water in 30 min and aged at room temperature for 2 hour. The solid was collected by filtration and washed with DMAc/water (1:2, 10 mL), water (10 mL) and heptane, and dried under vacuum with N$_2$ purge to give B-8 (1.26 g solid, ~90% isolated yield).

HPLC method: Ascentis R Express C18, 10 cm×4.6 mm, 2.7μ; standard gradient: 10-95% of B in 6 minutes (A=0.1% phosphoric acid, B=acetonitrile), 2 min hold, 2 min post; Flow rate: 1.8 ml/min; UV detection at 210 nm, 40° C.

| Compound | RT (min) |
| --- | --- |
| Compound B-7 | 3.96 |
| Compound B-8 | 4.41 |

14. Deprotection and Salt Formation

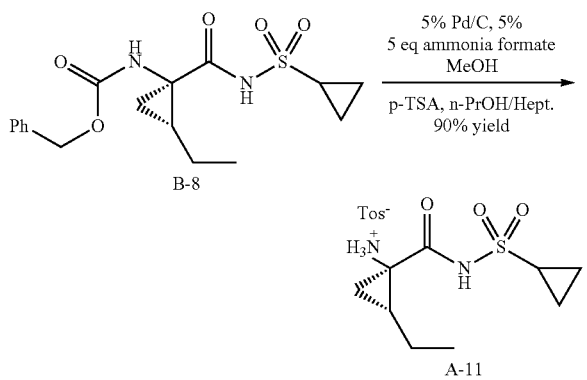

To a flask was charged Compound B-8 (2.12 g, 5.79 mmol), Pd/carbon (0.106 g, 5 wt %) and ammonium formate (1.82 g, 28.9 mmol) and MeOH (21 mL). The mixture was heated at 50° C. for 1-2 hours until HPLC shows full completion. The mixture was cooled to room temperature and filtered through CELITE and washed with MeOH 10 mL, and the filtrate was solvent switched n-PrOH and kept n-PrOH ~20 mL. The mixture in n-PrOH was heated to 60° C. and p-TSA (1.1 g, 5.79 mmol) was added. The mixture was stirred at 60° C. for 1 hour and cooled to room temperature. Heptane (10 mL) was added over 30 min, and the slurry was stirred for 2.5 hours and filtered. The cake was washed with n-PrOH/Heptane (2:1 10 mL) and dried to give ~90% yield salt product.

HPLC method: Ascentis R Express C18, 10 cm×4.6 mm, 2.7µ; standard gradient: 10-95% of B in 6 minutes (A=0.1% phosphoric acid, B=acetonitrile), 2 min hold, 2 min post; Flow rate: 1.8 ml/min; UV detection at 210 nm, 40° C.

| Compound | RT (min) |
| --- | --- |
| Compound B-8 | 4.41 |
| Compound A-11 | 1.03 |
| P-TsOH | 1.53 |

Example 2

Heterocycle Synthesis

Compound 3 was produced using the methods described in this example. The compounds and methods described in the example provide for different aspects and embodiments of the present invention.

1. Batch Reaction: Ortho-Lithiation of 3-Bromobenzonitrile and Formate Quench (1)

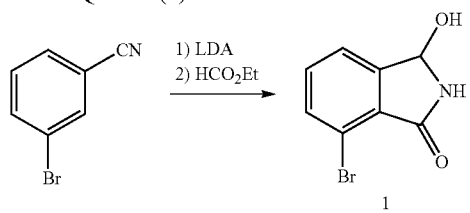

A 500 mL 3-neck round-bottom flask equipped with a mechanical stirrer, a thermocouple, a nitrogen inlet and a cooling bath was charged with the diisopropylamine (6.12 g, 8.61 mL, 60.4 mmol, 1.1 eq) and THF (50 mL). The mixture was cooled to −20° C., and n-butyllithium (24.17 mL, 60.4 mmol, 1.1 eq) was added, keeping the temperature below 0° C. The solution was aged 5 min, then cooled to −70° C. in $CO_2$/acetone.

To a separate, visually clean round-bottom flask was charged with 3-bromobenzonitrile (10 g, 54.9 mmol, 1.0 eq) and THF (20 mL). The solution of nitrile was transferred via cannula onto the lithium-amide solution, keeping the internal temperature below −65° C. The resultant solution was aged 5 min at −70° C.

Ethyl formate (6.04 mL, 74.2 mmol, 1.35 eq) was slowly added to the reaction mixture, keeping the internal solution below −65° C. The resultant solution was aged 5 min at −70° C.

The resultant solution was reverse quenched (added onto) ice-cold water (50 mL), keeping the internal temperature below 5° C. EtOAc (50 mL) was added followed by conc. HCl (9 mL) to afford a biphasic mixture with pH ~4. The mixture was transferred to a separatory funnel, and the aqueous layer removed, then back-extracted twice with EtOAc (50 mL). The combined organic layers were dried over $MgSO_4$, filtered and concentrated in vacuo to give 1 (11.63 g, 93% isolated yield).

HPLC Method: Column: Eclipse C18 Plus, 4.6×100 mm; (1.5 mL/min; 210 nm, 40° C., sample dissolved in MeCN/water. Mobile Phase A: 0.1% $H_3PO_4$ in water; Phase B: MeCN. Run gradient, from 20% B to 95% B over 5 min, hold 2 min.

| Compound | $R_t$ (min) |
| --- | --- |
| Ethyl Acetate | 1.67 |
| Iso-indanone 1 | 1.82 |
| 3-Bromo-benzonitrile | 3.62 |

1. Flow Reaction: Ortho-Lithiation of 3-bromobenzonitrile and Formate Quench (1)

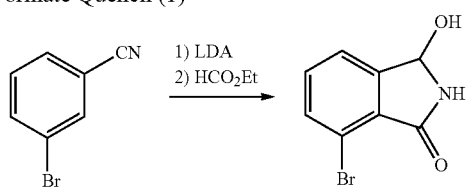

Stock solution A of 1.00 M diisopropylamine was prepared as follows: a 100 mL volumetric flask was charged with diisopropylamine (10.12 g, 14.25 mL, 100 mmol, 1.0 eq) and diluted with THF to a total volume of 100 mL. Stock solution B of LOOM 3-bromobenzonitrile was prepared as follows: a 100 mL volumetric flask was charged with 3-bromobenzonitrile (18.2 g, 100 mmol, 1.0 eq) and diluted with THF to a total volume of 100 mL. Stock solution C of 4.00M ethyl formate was prepared as follows: a 50 mL volumetric flask was charged with ethyl formate (14.8 g, 16.1 mL, 200 mmol, 1.0 eq) and diluted with THF to a total volume of 100 mL. Commercial n-butyllithium (40 mL, 100 mmol, 2.5M) was used as received, charged to a disposable plastic syringe and pumped via syringe pump. All other stock solutions were pumped via HPLC (Knauer) pumps, incorporating 100 psi back-pressure regulators between pump & reactor to ensure consistent flow rate.

HPLC Method: Column: Eclipse C18 Plus, 4.6×100 mm; (1.5 mL/min; 210 nm, 40° C., sample dissolved in MeCN/water. Mobile Phase A: 0.1% $H_3PO_4$ in water; Phase B: MeCN. Run gradient, from 20% B to 95% B over 5 min, hold 2 min.

| Compound | $R_t$ (min) |
| --- | --- |
| Ethyl Acetate | 1.67 |
| Iso-indanone (1) | 1.82 |
| 3-Bromo-benzonitrile | 3.62 |

2. Reduction of Iso-indanone to Iso-indole (2)

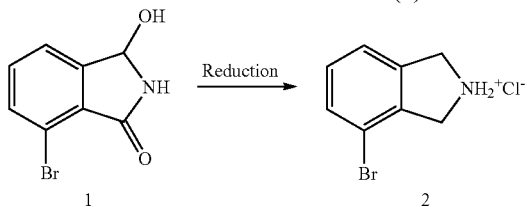

To a 50 mL round-bottom flask equipped with a magnetic stirrer, thermocouple, nitrogen inlet and reflux-condenser was charged with sodium borohydride (0.5 g, 13.16 mmol, 6 eq) and THF (10 mL). Boron trifluoride etherate (1.67 mL, 13.16 mmol, 6 eq) was added and the mixture was aged for 5 min at room temperature.

Crude iso-indanone (0.5 g, 2.193 mmol, 1 eq) was added to afford a slurry that was subsequently heated to 60° C. for 2 hours. After cooling to room temperature, the mixture was diluted with EtOAc (5 mL) then basified by addition of 50 wt % aqueous NaOH (~1.5 mL) to pH ~12. The biphasic mixture was transferred to a separatory funnel, and the aqueous layer was removed. The organic layer was collected, dried over MgSO$_4$, filtered & concentrated in vacuo to 265 mg of 2, 60% isolated yield.

HPLC Method: Column: Eclipse C18 Plus, 4.6×100 mm; (1.0 mL/min; 210 nm, 40° C., sample dissolved in MeCN/water. Mobile Phase A: 0.1% H$_3$PO$_4$ in water; Phase B: MeCN. Run gradient, from 5% B to 95% B over 20 min, hold 5 min.

| Compound | $R_t$ (min) |
| --- | --- |
| Iso-indanone (1) | 7.1 |
| Reduced iso-indoline (2) | 7.5 |
| 3-Bromo-benzonitrile | 13.0 |

3. Kumada Coupling of Bromo-iso-indole

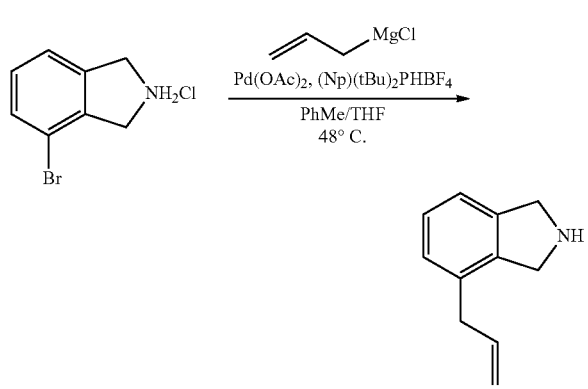

A 3-neck flask with overhead stirring was purged three times with vac/N$_2$ backfill. Under positive N$_2$ pressure, the flask was charged with the bromoisoindoline HCl salt (25 g, 106.6 mmol), Pd(OAc)$_2$ (0.199 g, 0.533 mmol), and the ligand (di-tert-butylneopentylphosphonium tetrafluoroborate, 0.325 g, 1.066 mmol). PhMe (toluene) (450 mL, deoxygenated via sparging with N$_2$) was then added, and the resulting slurry was then cooled to T$_i$=5° C. using an external bath. Allylmagnesium chloride (1.7 N in THF, 207 mL, 351.8 mmol) was charged to an addition funnel via cannula, and then added at a rate such that T$_i$<20° C. The resulting solution was then was heated to T$_i$=45-50° C.

After 16 hours, LC showed >99% conversion of starting material. The reaction was cooled to room temperature, and then was inverse-quenched into 250 mL of 15% aqueous citric acid. The phases were separated, and the aqueous phase containing the product was held while the dark organic phase was rejected. The extractor that contained the aqueous phase was charged with 125 mL of PhMe. The pH of the aqueous phase was adjusted by the addition of 115 mL of NH$_4$OH. The phases were separated, and the organic phase containing the product was held while the aqueous phase was rejected. The organic phase was washed with 20 mL of 15% aqueous NaCl. The PhMe solution was concentrated with azeotrope to a 10 volume solution (KF<2000 ppm H$_2$O).

This PhMe solution of product was transferred to 250 mL flask with overhead stirring. An addition funnel was charged with 17.5 mL of 5.33 M HCl in IPA (5.3 M), which was added slowly over 20 minutes. The resulting slurry was aged for 30 minutes at T$_i$=40° C., and then was gradually cooled to T$_i$=20-22° C. over 30 minutes. After aging for 1 hour, the slurry was slowly cooled to T$_i$=0° C. over 30 minutes by use of an external bath. After 30 minutes, the slurry was filtered. The cake was washed with 16 mL of cold (T$_i$=−10 vC) 14:2 PhMe:IPA. The cake was then washed with 15 mL of ambient temperature (T$_i$=22° C.) MTBE. After drying, 7.6 g of allyl isoindoline was isolated as an off white solid. The isolated product assayed for 98.7 wt %.

Example 3 tert-Leucine Unit

Compound 6 was produced using the methods described in this example. The compounds and methods described in the example provide for different aspects and embodiments of the present invention.

Alkylation of Ethyl Isobutyrate with Allyl Bromide (4)

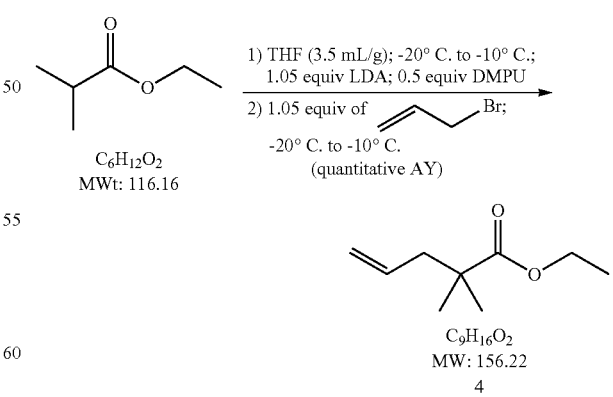

A 2 L 3-necked RB flask is charged with THF (406 mL), diisopropylamine (157 mL, 111 g, 1.1 moles) and is cooled to around −30° C. n-Hexyllithium (2.3M/Hexane, 457 mL, 1.05 moles) is added over 15 minutes at −20° C. to −10° C., and is aged for an additional 10 minutes after completion of the addition. Ethyl isobutyrate (135 mL, 116 g, 1.0 mole) is added over 15 minutes keeping the temperature between −5° C. and −10° C. At the end of addition, DMPU (60.3 mL, 64.1 g, 0.5 mole) is added over a couple of minutes, and the resulting solution is aged at −10° C. to −20° C. for 15 minutes. Allyl bromide (91 mL, 127 g, 1.05 moles) is then added dropwise over 15-30 minutes keeping the temperature around −10° C. The resulting solution (LiBr out of solution) is allowed to warm to room temperature and reverse quenched into a biphasic mixture of n-heptane (696 mL, 6 volumes) and 2.5N aqueous HCl (580 mL). Layers are separated (pH∼1-2), and the organic layer is washed with water (2×348 mL, 2×3 volumes). The organic layer is then distilled to remove most of the solvent (THF, Hexane, Heptane) at an internal temperature comprised between +50° C. and +60° C., and a pressure between +250 and +400 mm Hg. Distillation is stopped when concentration is ca. 1 molar (156 g/L). Crude yellow concentrate is used as is in the next step.

GC Method: Column: capillary; stationary phase: HP-1 methyl siloxane (30 m×250 μm×0.25 μm); detector: FID; Carrier gas: He 3.0 mL/min, constant flow [P∼25 psig]; oven Temp=50° C. hold 3 min, then 20° C./min to 280° C.; Injector Temp=250° C.; detector Temp=300° C.; Detector gas flow: $H_2$ @ 40 mL/min; Air @ 400 mL/min; Make-up gas: He @ 25 mL/min.

| Compound | $R_t$ (min) |
|---|---|
| Ethylisobutyrate | 0.91 |
| Alllyl ethyl isobutyrate 4 | 4.55 |

VITRIDE® Reduction—Preparation of 2,2-dimethyl-pent-4-en-1-ol (5)

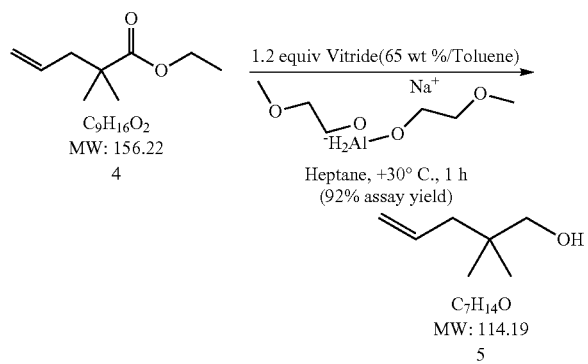

A 2 L RB flask was charged with a ca. 1M heptane solution of crude allylester (156.2 g assay, 1.0 mole in ca. 740 mL of heptane), and was cooled to around +10° C. VITRIDE® 311 g, 301 mL, 12 moles) was added over 30 min keeping the internal temperature between +30 and +35° C. The batch was aged for 1 hour at +30° C., cooled to +10° C. and hydrolyzed by the slow addition of IPA (77 mL) over 5 min. The reaction mixture was reversely quenched at room temperature into 6N HCl (1350 mL) over cooling keeping temperature below +30° C. Biphasic mixture was aged at ambient temperature for 1 hour, and layers were separated. Organic layer was washed with water (2×500 mL), and was concentrated under reduced pressure (35 mmHg @ 25° C.). Crude concentrate product (105 g assay, 92% AY) was used as is in the next step.

GC Method: Column: capillary; stationary phase: HP-1 methyl siloxane (30 m×250 μm×0.25 μm); detector: FID; Carrier gas: He=3.0 mL/min, constant flow [P∼25 psig]; oven Temp=50° C. hold 3 min, then 20° C./min to 280° C.; Injector Temp=250° C.; detector Temp=300° C.; Detector gas flow: $H_2$ @ 40 mL/min; Air @ 400 mL/min; Make-up gas: He @ 25 mL/min.

| Compound | $R_t$ (min) |
|---|---|
| IPA | 1.15 |
| Toluene | 1.99 |
| Alcohol 5 | 3.13 |
| Allyl ethyl isobutyrate 4 | 4.55 |
| Unknown | 6.97 |

Carbamate/Leucine Formation—CHA (Cyclohexylamine) Salt Preparation (6)

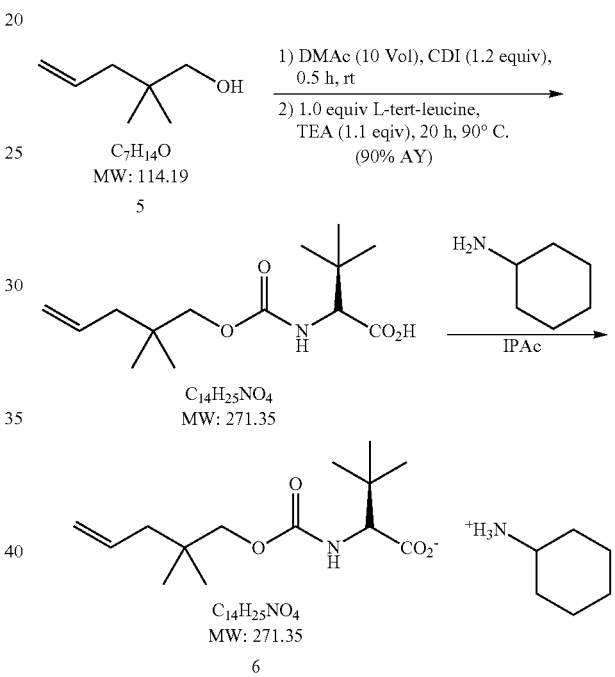

Procedure A

A 50 mL RB flask is charged with DMF (18 mL) and the crude alcohol (5.179 g, ca. 45-50 wt %, ca. 2.4 g assay, 18.7 mmol), and was cooled to around +10° C. CDI (3.0 g, 18.7 mmol) is added portion wise over 15 min. The resulting homogeneous mixture was stirred at ambient temperature for 30 min.

L-tert-leucine (2.45 g, 18.7 mmol) was added in one portion followed by the addition of triethylamine (2.85 mL, 20.5 mmol). The resulting slurry was heated to 90° C. for 12 hours, and allowed to cool to room temperature. The solution was partitioned between n-heptane (15 mL), and water (18 mL). Layers were separated, and the organic layer was discarded.

The DMF aqueous basic layer was partitioned with MTBE (22 mL) and was neutralized to pH∼1-2 with (12 N) conc. HCl solution (ca. 5.5 mL). Layers were separated, and the organic layer was washed with water (2×15 mL). The organic solution was concentrated, switched to acetonitrile to dry to KF<500 ppm. Resulting crude carbamate was placed in a 100 mL flask, dissolved in acetonitrile (65 mL), and heated to 45° C. Dicyclohexylamine (3.72 mL, 18.7 mmol) was added over 1 hour to crystallize the salt. The slurry was stirred at 45° C. for 2 hours, and was allowed to cool ambient temperature, filtered, and rinsed with acetonitrile (10 mL). The resulting white salt is dried at 45° C. in the oven for 24 hours to give 6.1 g of product (74% overall yield).

Procedure B

A 50 mL RB flask is charged with DMF (18 mL) and the crude alcohol (5.179 g, ca. 45-50 wt %, ca. 2.4 g assay, 18.7 mmol), and was cooled to around +10° C. CDT (3.0 g, 18.7 mmol) is added portion wise over 15 min. The resulting homogeneous mixture was stirred at ambient temperature for 30 min.

L-tert-leucine (2.45 g, 18.7 mmol) was added in one portion followed by the addition of triethylamine (2.85 mL, 20.5 mmol). The resulting slurry was heated to 90° C. for 12 hours, and allowed to cool to room temperature. The solution was partitioned between n-heptane (15 mL), and water (18 mL). Layers were separated, and the organic layer was discarded.

Resulting crude carbamate was placed in a 100 mL flask, dissolved in IPAc (65 mL), and heated to 45° C. Cyclohexylamine (3.72 mL, 18.7 mmol) was added over 1 hour to crystallize the salt. The slurry was stirred at 45° C. for 2 hours, and was allowed to cool ambient temperature, filtered, and rinsed with IPAc (10 mL). The resulting white salt is dried at 45° C. in the oven for 24 hours to give 6.1 g of product (74% overall yield).

Example 4

Diene-Esters

Diene-esters were produced using the methods described in this example. The compounds and methods described in the example provide for different aspects and embodiments of the present invention.

Diene-Ester Formation

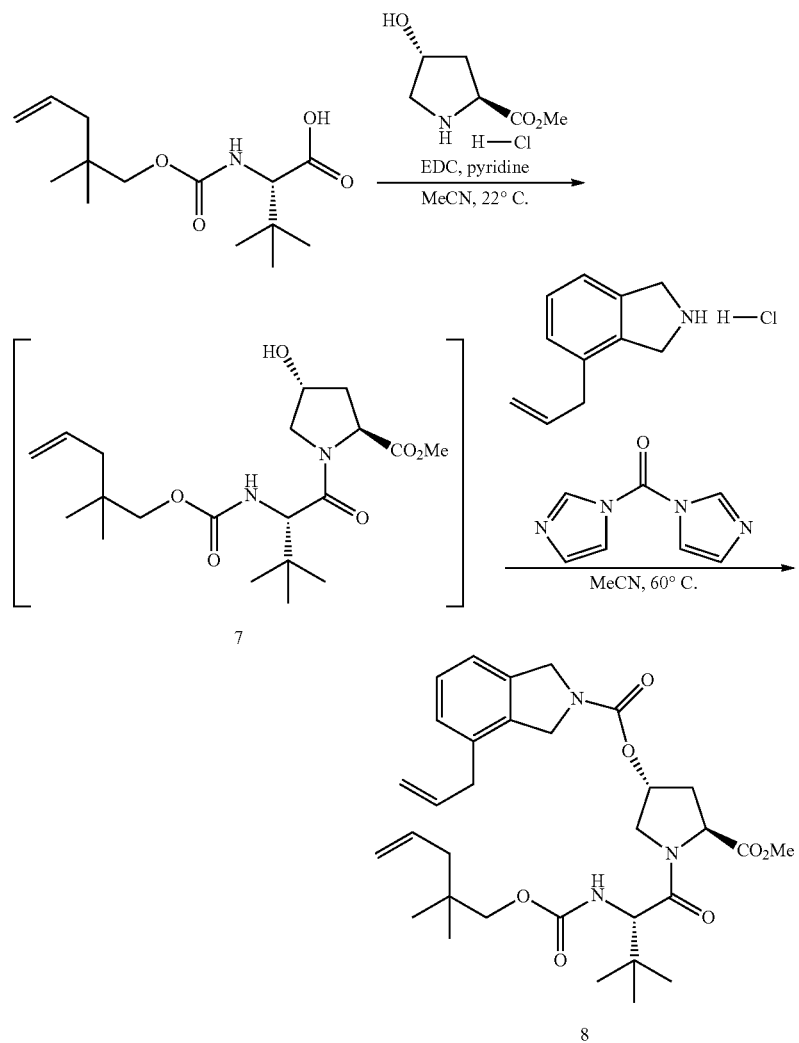

The DMF aqueous basic layer was partitioned with MTBE (22 mL) and was neutralized to pH~1-2 with (12 N) cone. HCl solution (ca. 5.5 mL). Layers were separated, and the organic layer was washed with water (2×15 mL). The organic solution was concentrated, switched to IPAc to dry to KF<500 ppm.

A 100 mL flask with overhead stirring was charged with the "ene-acid" (5.0 g, 18.43 mmol) followed by MeCN (KF=135 ppm). trans-4-Hydroxy-L-proline methyl ester hydrochloride (3.87 g, 95 W %, 20.26 mmol) was charged, followed by pyridine (1.6 g, 20.27 mmol). After a 45 minute age, EDC- HCl (4.42 g, 23 mmol) was charged as a solid in a single portion. After 3.5 h, LC showed >98% conversion to the desired product.

CDI (3.45 g, 21.2 mmol) was added. The reaction was then heated to $T_i$=55° C. After 1 hour, LC showed considerable improvement but still incomplete alcohol activation (LCAP ratio of imidazole carbamate:sm=80:20). After 4 hours, <97% conversion was observed. At this point, 1.4 equiv of 4-allylisoindoline HCl salt (5.05 g, 21.2 mmol) was added and the reaction was stirred overnight at $T_i$=55-60° C.

After 16 hours, the homogeneous reaction mixture was inverse quenched into 60 mL of water and 40 mL of MTBE. The aqueous phase was rejected, and the organic phase was washed with 50 mL of 15% citric acid (39 mmol of citric acid). The organic phase was washed with 15 mL of 4% aq. Na₂CO₃ then 10 mL of H₂O. The organic phase was dried and assayed for 9.09 g of desired product (15.58 mmol, 84.5% AY).

"Diene-K Salt" Formation

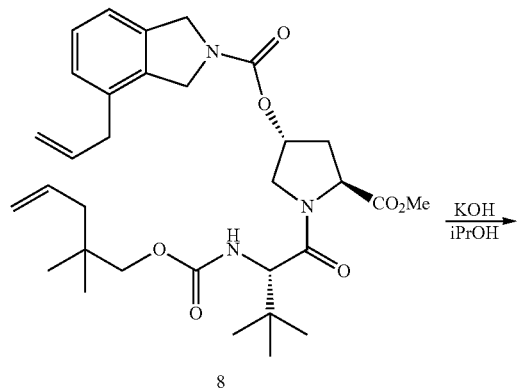

8

To the "diene ester" (9.09 g, 15.57 mmol) in 100 mL IPA (KF<1000 ppm) was added solid KOH (85 W %, 1.44 g, 21.8 mmol). After 1.5 hours, the solution was treated with 50 mg of seed, and the resulting slurry was aged for 16 hours.

The slurry was then filtered, and washed with 30 mL of iPrOH. The cake was dried with suction, from which was isolated 8.81 g of diene acid potassium salt.

"Diene-Acid" Formation

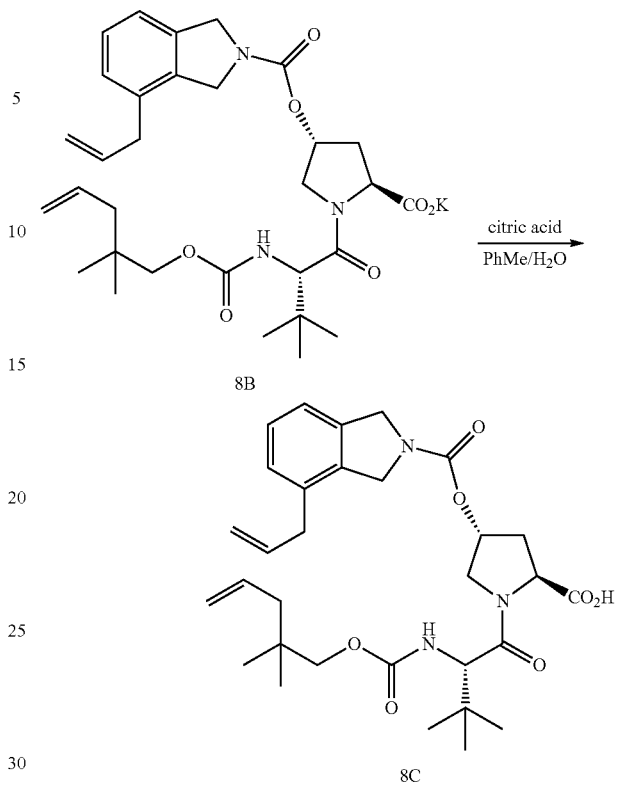

To a 250 mL flask was charged with the "diene-K salt" (9.5 g, 15.63 mmol) in 75 mL of PhMe. 35 mL of 15% citric acid (27.3 mmol of citric acid) was added. After 1 hour, the phases were separated. The organic phase was washed with 10 mL of H₂O. The organic phase was dried via azeotrope with PhMe under constant volume conditions, then filtered and concentrated.

Example 5

Marcolactam Formation (Compound A)

Compound A (also referred to herein as Compound 12) was produced using the methods described in this example. The compounds and methods described in the example provide for different aspects and embodiments of the present invention.

RCM with Diene-Acid

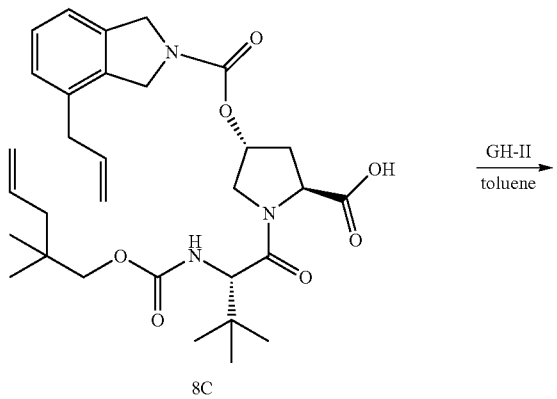

-continued

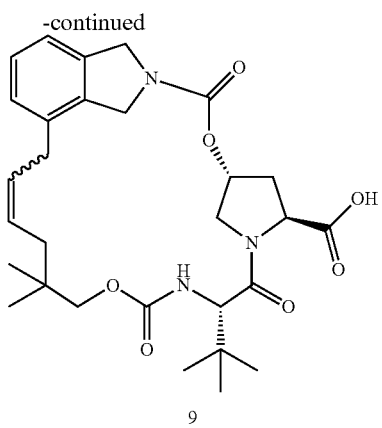

9

-continued

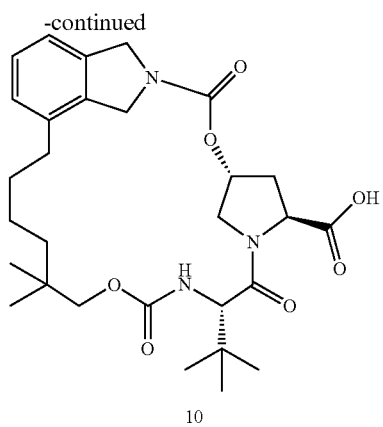

10

A 500 mL three neck RB flask with reflux condenser was charged with 1,6-dichloroquinone (0.105 g, 0.595 mmol) and toluene (170 mL, 10 Vol) at room temperature. The reaction solution was heated to 107° C. with gentle nitrogen gas bubbling. In the meantime, diene-acid (16.94 g, 29.7 mmol) in toluene stock solution (45 wt %) was diluted with 17 mL of degassed toluene and Grubbs-Hoveyda-II catalyst (0.037 g, 0.059 mmol) was dissolved in 17 mL of degassed toluene. 10 v % of diene-acid stock solution was added into the reaction vessel. When the reaction temperature reached around 107° C., the remaining diene-acid stock solution and Grubbs-Hoveda $2^{nd}$ generation catalyst were simultaneously added to reaction solution for 58 minutes and 60 minutes, respectively. After the addition of catalyst was completed, the reaction mixture was stirred for one more hour to achieve the complete consumption of diene-acid substrate. The reaction mixture was cooled to room temperature. The toluene solution was transferred to High-Pressure-Lab for hydrogenation.

HPLC Conditions: Ascentis Express C18 (150 mm×4.6 mm; 2.7 um), 1.0 mL/min, detection @220 nm. 40° C., standard gradient: 0 min: 40% of B, 15 min: 95% B, 20 min: 95% B, 20.1 min: 40% B (A=Water with 0.1% $H_3PO_4$, B=Acetonitrile).

19-Membered RCM-Ester-Product: 7.986 min (cis) and 8.137 min (trans).

RCM-Acid Desired product: 8.917 min (cis) and 9.236 min (trans).

Diene-Acid Starting material: 11.252 min.
Cyclic dimers: 12.436 min (Broad).

Hydrogenation of RCM-Acid Product

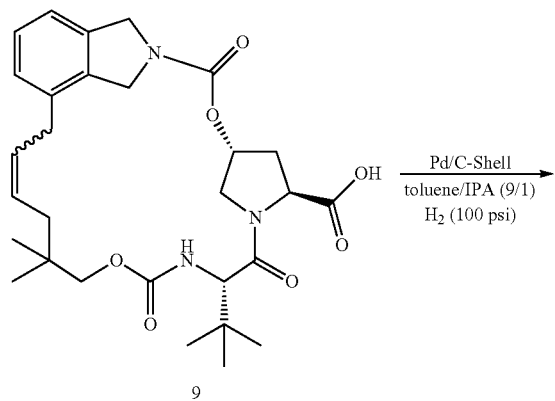

9

The RCM-Acid product in toluene (17.0 g, 31.4 mmol) was transferred to high-pressure reactor and the residue was washed with 25.5 mL IPA and transferred to reactor. 20 wt % of 5% Pd/C-Shell catalyst was added to the reaction solution. The reaction vessel is purged three times with nitrogen gas followed by three purges of hydrogen gas at 100 psi. The reaction mixture was stirred for 24 hours under 100 psi hydrogen. After the reaction was completed, the catalyst was filtered and washed with IPA (410 mL, 5 vol). Solvent was switched to IPA (300 mL, 3 vol) for crystallization.

Crystallization Procedure 0.56 mL IPAc was added to the crude Mac-Acid stock solution in IPA. Then the dark brown solution is heated to 40° C. and aged over 15 minutes at 40° C. 1.78 mL DI water was slowly added into the hot solution over 10 min at 40° C., and the resulting solution was further stirred over 15 minutes. The solution was cooled down to 22° C. At that point, 1 wt % of seed was added to the homogeneous solution. Then the solution was slowly cooled down to 0° C. over 3 hours.

The slurry was aged for 14 hours at 0° C. The slurry was filtered at cold room (around 3° C.) and washed with 0.75 mL of pre-cooled IPA-water two times. The solid was dried over 24 hours at 45° C. under vacuum (~30 mmHg). 650 mg of the desired product (40% isolated yield from crude Mac-Acid) was obtained as a white solid with over 99% HPLC purity.

HPLC Conditions: Ascentis Express C18 (150 mm×4.6 mm; 2.7 um), 1.0 mL/min, detection @220 nm. 40° C., standard gradient: 0 min: 40% of B, 15 min: 95% B, 20 min: 95% B, 20.1 min: 40% B (A=Water with 0.1% $H_3PO_4$, B=Acetonitrile).

19-Membered Mac-Ester: 8.382 min.
Mac-Acid Desired product: 9.614 min.
Cyclic dimers: 13.185 min.

Hydrolysis

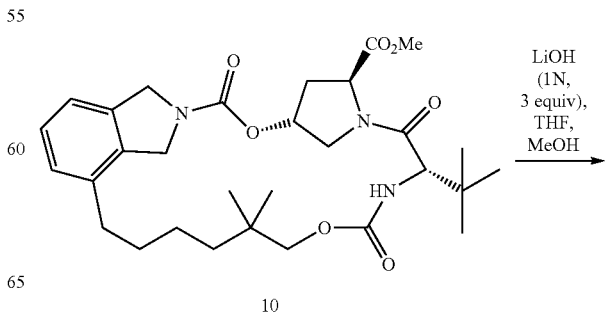

10

-continued

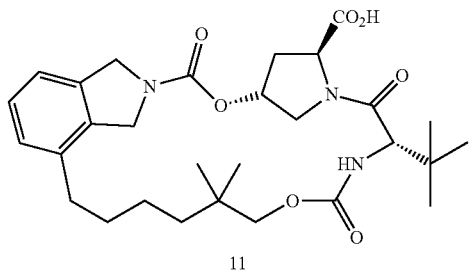

11

A 100-L extraction vessel equipped with overhead stirrer and thermocouple was charged with a solution of ester (17.8 g, 31.91 mmol) in THF (96 mL) and cooled to 5° C. An aqueous solution of lithium hydroxide (1N, 96 mL, 96 mmol) was added dropwise via addition funnel over 30 minutes keeping the temperature below 15° C. With the same addition funnel, methanol was added over 10 minutes at 15° C., after which the white, heterogeneous mixture was allowed to warm to room temperature. Upon warming, the solution becomes homogeneous. After ca. 30 minutes, the solution turns from light yellow to dark brown. The reaction, sampled at this time, is judged complete by HPLC analysis (>99.9 A % conversion).

The batch was cooled to 5° C. and treated with 1N HCl (112 mL) to quench the excess LiOH. After addition, the solution was warmed to 20° C. and diluted with IPAc (180 mL, 10 vol). After agitating for 15 minutes, the layers are allowed to separate and the organic layer is collected (170 g, 98% Assayed yield).

The IPAc solution (~340 mL) was treated with Darco KB-G (40 wt %, 7 g) at 20° C. for 10 minutes, and the solution was filtered through SOLKA-FLOC followed by filtration through a 5 um in-line filter (170 g, >99% recovery). The IPAc solution was concentrated under reduced pressure, keeping the temperature below 25° C., to 100 mL. An additional 100 mL of IPAc was added and the batch was concentrated to 100 mL. The solution was diluted with DMF (80 mL) and the concentration was continued until the final batch volume is 80 mL. The batch was diluted with DMF (20 mL) and IPAc (80 mL).

HPLC Method: Column: Ace 3 C8 (3 mm×150 mm, 3 μm) (0.75 mL/min; 215 nm, 35° C., sample dissolved in MeCN/water. Mobile Phase A: 0.1% $H_3PO_4$ in water; Phase B: MeCN. Run gradient, from 20% B to 90% B over 12 min, hold 3 min.

| Compound | $R_t$ (min) |
|---|---|
| Acid 11-epi | 9.89 |
| Acid 11 | 10.05 |
| Ester 10-epi | 10.97 |
| Ester 10 | 11.13 |
| dimer | 11.74 |

Coupling (HOBt)

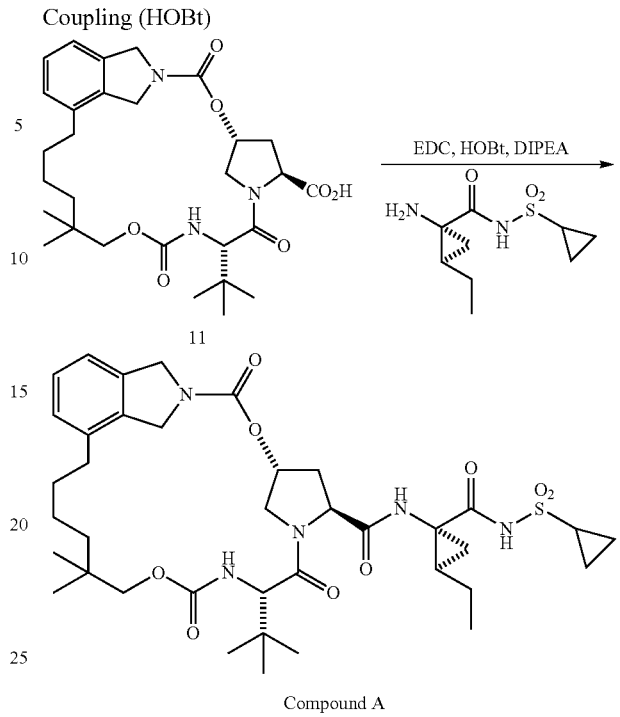

Compound A

A 1-L flask equipped with an overhead stirrer, nitrogen inlet, thermocouple was charged with macrocyclic acid solution (16.8 g, 30.8 mmol) in 168 mL IPAc. The solution was set stirring and the tosylate P1 piece (14 g, 34.6 mmol) was added as a solid. Upon dissolution (<10 min), HOBt (4.7 g, 31 mmol) was added as a solid. The batch was cooled to 15° C. and DIPEA (8.0 g, 61.8 mmol) was added via addition funnel while maintaining the temperature below 20° C. Solid EDC HCl (8.3 g, 43 mmol) was added. No change in temperature was observed. After 3 hours, the reaction was judged complete by HPLC (>99.8 A % conversion, 91% assayed yield, 210 g).

The batch was transferred to a 1-L extraction vessel, cooled to 10° C., diluted with IPAc (16.8 L) and water (33.6 L). The mixture was agitated for 10 minutes. The layers were allowed to separate, and the aqueous layer discarded (pH=6-7). Aqueous HCl (1 N, 168 mL) was added to the IPAc layer and the solution was agitated for 10 minutes. The layers were allowed to separate, and the aqueous layer discarded (pH=1-2). The IPAc solution was then treated with water/brine (150 mL/170 mL). After 10 minute agitation, the layers were allowed to phase separate, and the aqueous layer was discarded (pH=2-3). The IPAc solution was concentrated and flushed with ethanol (500 mL) until there is 2.5 mol % IPAc in ethanol, as judged by 1H NMR spectroscopy. Yield=202 g, 87% assayed yield.

HPLC Method: Column: Ace 3 C8 (3 mm×150 mm, 3 μm) (0.75 mL/min; 215 nm, 35° C., sample dissolved in MeCN/water. Mobile Phase A: 0.1% $H_3PO_4$ in water; Phase B: MeCN. Run gradient, from 20% B to 90% B over 12 min, hold 3 min.

| Compound | $R_t$ (min) |
|---|---|
| Acid 11-epi | 9.89 |
| Acid 11 | 10.05 |
| Amide 12-epi | 11.10 |
| Amide 12 | 11.27 |

-continued

| Compound | R$_t$ (min) |
|---|---|
| Dimer | 12.99 |

Alternative Coupling (EDC-Pyridine)

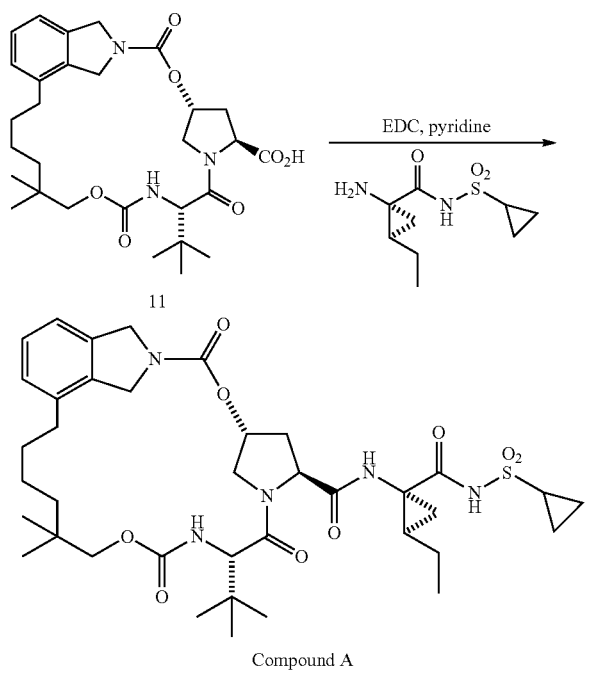

Compound A

Recrystallization of Compound A

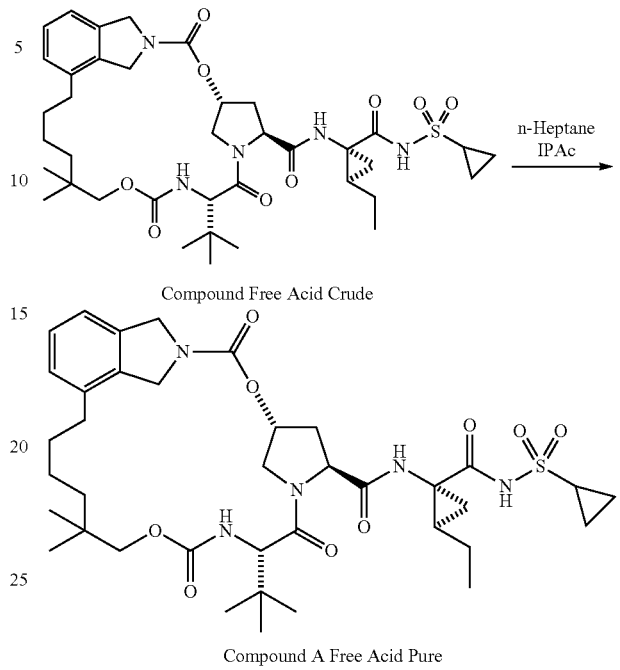

A 250 mL 3-neck round bottom flask equipped with magnetic stirrer, nitrogen inlet and thermocouple was charged with macrocyclic acid (62.55 g, 26.9 mmol) in IPAc (16 mL) and MeCN (36 mL) to ensure complete transfer. Aminetosylate (11.44 g, 28.3 mmol) and pyridine (3.27 mL, 40.5 mL) were added to the mixture, to afford an off-white slurry. The resultant slurry was degassed by purging nitrogen subsurface for 5 min. EDC-HCl (6.72 g, 35.0 mmol) was added to the flask at room temperature. After ~15 min, the slurry was observed to become a clear, amber solution. The solution was aged at room temperature with continuous sub-surface N$_2$-purging to prevent oxidative degradation. A very slight exotherm of 1-2° C. was observed upon addition of EDC-HCl. Aliquot of the crude reaction mixture 5 min after addition was complete showed 80% conversion. Aliquot of the crude reaction mixture 75 min after addition was complete showed >99% conversion. IPAc (45 mL) and DI-water (45 mL) were added to the reaction mixture to afford a biphasic mixture. The mixture was transferred to a separatory funnel, and after vigorous mixing, the aqueous (bottom) layer was removed. The organic phase was washed with 1N HCl, then filtered over SOLKA-FLOC and concentrated in vacuo, flushing with IPAc (2×100 mL) to azeotrope out any residual water. The material was concentrated to 40.0 g light yellow oil, which was determined by HPLC analysis to be 49 wt % amide A (96% assay yield).

A seed bed was prepared by charging 18 ml IPAc (1 vol) and 24 ml n-Heptane (1.25 vol) to create a 57:43 v/v mix. 1.9 g anhydrous Compound A (PSD—MV>16 um, if MV is <16 um, an alternative seed ripening procedure is provided below) was then charged to the Heptane/IPAc mix, agitated at 15-25° C. and allowed to turnover for 30 minutes to form Compound A Heptane solvate. The seed bed may be wet milled using an IKA mill (fine/superfine rotor-stator, 40-60 turnovers). The seed bed is then warmed to 50° C.

Seed ripening: 1.9 g anhydrous dry cake was charged to 21 ml of n-Heptane/IPAc at 45/55 (v/v) forming a slurry and agitated for at least 30 minutes in order to turn over into heptane solvate. Slurry was brought to 55-65° C. where 11.4 ml of n-Heptane was charged over 3 hours to the slurry. Once complete, 4.7 ml of dry IPAc is charged, bringing the slurry to 47 g/L concentration and 57/43 v/v Heptane/IPAc. The bed was then cooled to 45° C. over at least 12 hours and then to ambient over at least 3 more hours. The seed bed may then be milled as necessary.

Alternatively, a seed bed may be prepared from a final crystallization slurry from a previous run. Reserve 27 ml of post crystallization slurry (~70 g/L. 1.9 g assay, 65/35 (v/v) n-Heptane/IPAc). Add 5.6 ml n-Heptane and 7.7 ml dry IPAc and agitate. Target slurry composition is 47 g/L and 57/43 v/v n-Heptane/IPAc. Bed is then milled as above and heated to 50° C.

Over 12 hours, 92 ml of Compound A crude stream in IPAc (coupling product, 87% assay volume IPAc, 18.67 g assay) was added into the 50° C. seed bed. Simultaneously, 103 ml (5.8 vol) of n-Heptane was added into the seed bed to maintain 57:43 v/v Heptane/IPAc. At the end of the 12 hour addition, an additional 52 ml of n-Heptane was added over 3 hours, pushing the Heptane:IPAc ratio to 65/35 v/v. Once heptane addition was complete, the batch was cooled to 20° C. over 3 hours and filtered.

Cake washes consist of one wash of 37 ml (2 vol) 65/35 v/v n-Heptane/IPAc mix. Two more washes of 37 ml each (2 vol each) of pure n-heptane follow. Wet cake (Compound A Heptane solvate) was then blown dry of the bulk liquors and dried at 70° C. under vacuum to generate Compound A free acid anhydrate.

Other embodiments are within the following claims. While several embodiments have been shown and described, various modifications may be made without departing from the spirit and scope of the present invention.

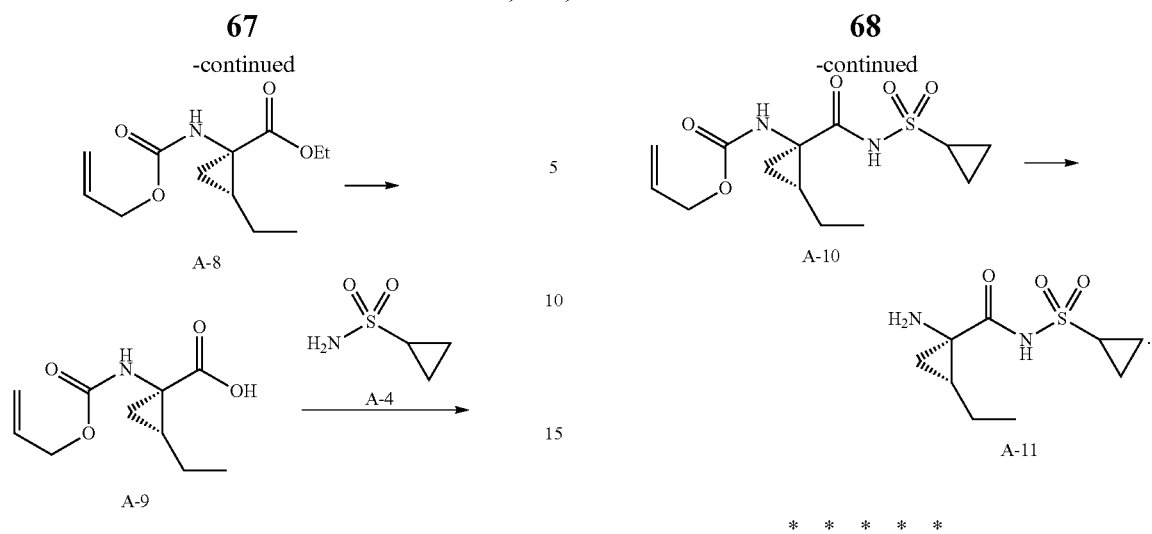

What is claimed is:

1. A compound selected from the group consisting of:

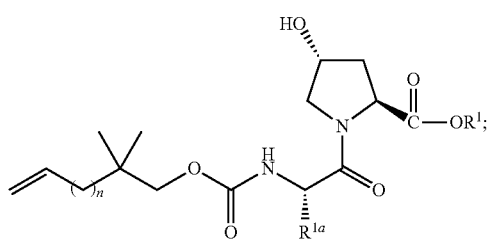

(Formula I)

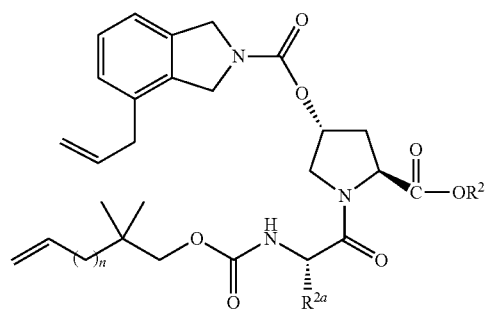

(Formula II)

or a salt thereof; and

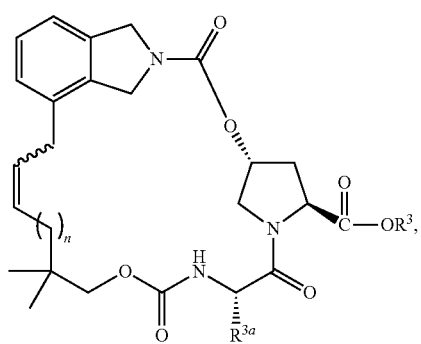

(Formula III)

or a salt thereof;
wherein $R^1$ is either a $C_{1-6}$ alkyl, $C_3$-$C_8$ cycloalkyl, or Aryl;
$R^2$ and $R^3$ are each either H, $C_{1-6}$ alkyl, $C_3$-$C_8$ cycloalkyl, or Aryl;
$R^{1a}$, $R^{2a}$, and $R^{3a}$ are each either $C_{1-6}$ alkyl or $C_3$-$C_8$ cycloalkyl;
n is 0-5;
Aryl is either phenyl, substituted phenyl, naphthyl, or substituted naphthyl, provided that substituted phenyl and substituted naphthyl each have 1 to 5 substituents independently selected from the group consisting of:

(1) $C_{1-6}$ alkyl,
(2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, $N(R^A)C(O)R^B$, $N(R^A)CO_2R_B$, $N(R^A)SO_2R^B$, $N(R^A)SO_2N(R^A)R^B$, $OC(O)N(R^A)R^B$, $N(R^A)C(O)N(R^A)R^B$, or $N(R^A)C(O)C(O)N(R^A)R^B$,
(3) O—$C_{1-6}$ alkyl,
(4) $C_{1-6}$ haloalkyl,
(5) O—$C_{1-6}$ haloalkyl,
(6) OH,
(7) halogen,
(8) CN,
(9) $NO_2$,
(10) $N(R^A)R^B$,
(11) $C(O)N(R^A)R^B$,
(12) $C(O)R^A$,
(13) $C(O)$—$C_{1-6}$ haloalkyl,
(14) $C(O)OR^A$,
(15) $OC(O)N(R^A)R^B$,
(16) $SR^A$,
(17) $S(O)R^A$,
(18) $SO_2R^A$,
(19) $SO_2N(R^A)R^B$,
(20) $N(R^A)SO_2R^B$,
(21) $N(R^A)SO_2N(R^A)R^B$,
(22) $N(R^A)C(O)R^B$,
(23) $N(R^A)C(O)N(R^A)R^B$,
(24) $N(R^A)C(O)C(O)N(R^A)R^B$, or
(25) $N(R^A)CO_2R^B$; and
$R^A$ and $R^B$ are each independently H or $C_{1-6}$ alkyl.

2. The compound of claim 1, wherein said compound has the structure:

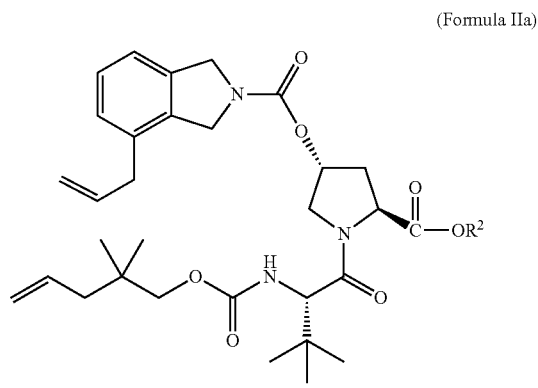

(Formula IIa)

or a salt thereof.

3. The compound of claim 2, wherein said compound has the structure:

(Formula II)

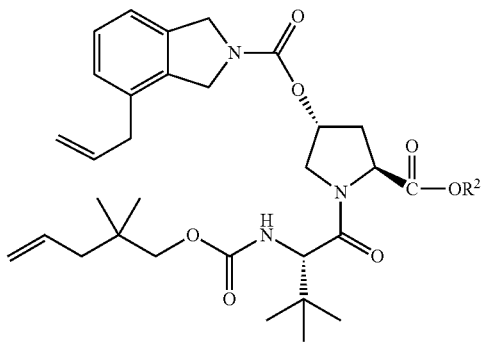 [SMILES: C=CCc1cccc2c1CN(C(=O)O[C@@H]1C[C@@H](C(=O)O)N(C(=O)[C@@H](NC(=O)OCC(C)(C)CC=C)C(C)(C)C)C1)C2]

or a salt thereof and R² is a H or $C_{1-6}$ alkyl.

4. The compound of claim 3, wherein said compound is a salt of:

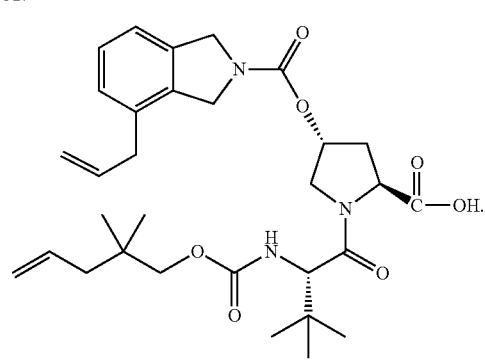

5. The compound of claim 4, wherein said compound is:

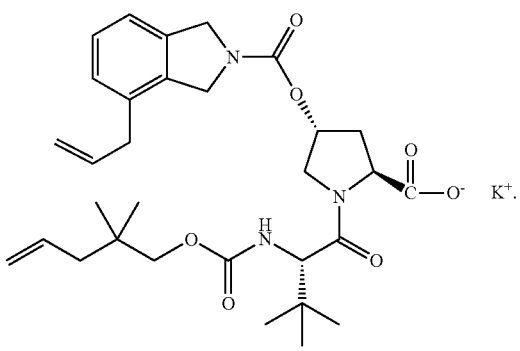 [SMILES: C=CCc1cccc2c1CN(C(=O)O[C@@H]1C[C@@H](C(=O)[O-])N(C(=O)[C@@H](NC(=O)OCC(C)(C)CC=C)C(C)(C)C)C1)C2]

6. A method of making the Formula IIa compound of claim 2, comprising the step of coupling (Formula Ia)

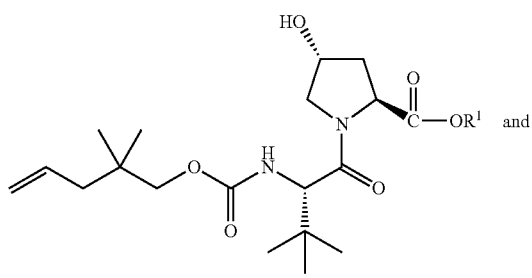 and

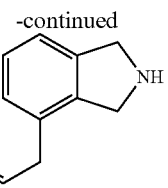

or salt thereof to form (Formula IIa)

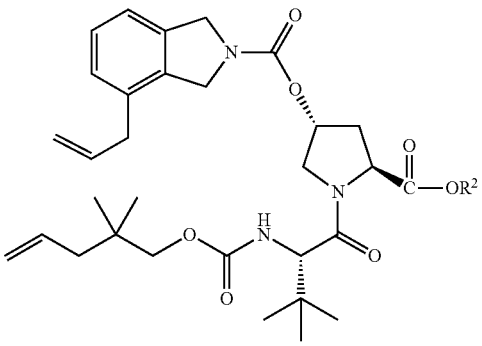

or a salt thereof; wherein
  R¹ is either a $C_{1-6}$ alkyl, $C_3$-$C_8$ cycloalkyl, or Aryl;
  R² is either H, $C_{1-6}$ alkyl, $C_3$-$C_8$ cycloalkyl, or Aryl;
  Aryl is either phenyl, substituted phenyl, naphthyl, or substituted naphthyl, provided that substituted phenyl and substituted naphthyl each have 1 to 5 substituents independently selected from the group consisting of:
  (1) $C_{1-6}$ alkyl,
  (2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, $N(R^A)C(O)R^B$, $N(R^A)CO_2R_B$, $N(R^A)SO_2R^B$, $N(R^A)SO_2N(R^A)R^B$, $OC(O)N(R^A)R^B$, $N(R^A)C(O)N(R^A)R^B$, or $N(R^A)C(O)C(O)N(R^A)R^B$,
  (3) O—$C_{1-6}$ alkyl,
  (4) $C_{1-6}$ haloalkyl,
  (5) O—$C_{1-6}$ haloalkyl,
  (6) OH,
  (7) halogen,
  (8) CN,
  (9) $NO_2$,
  (10) $N(R^A)R^B$,
  (11) $C(O)N(R^A)R^B$,
  (12) $C(O)R^A$,
  (13) C(O)—$C_{1-6}$ haloalkyl,
  (14) $C(O)OR^A$,
  (15) $OC(O)N(R^A)R^B$,
  (16) $SR^A$,
  (17) $S(O)R^A$,
  (18) $SO_2R^A$,
  (19) $SO_2N(R^A)R^B$,
  (20) $N(R^A)SO_2R^B$,
  (21) $N(R^A)SO_2N(R^A)R^B$,
  (22) $N(R^A)C(O)R^B$,
  (23) $N(R^A)C(O)N(R^A)R^B$,
  (24) $N(R^A)C(O)C(O)N(R^A)R^B$, or
  (25) $N(R^A)CO_2R^B$; and
  $R^A$ and $R^B$ are each independently H or $C_{1-6}$ alkyl.

7. The method of claim 6, wherein $R^1$ is $C_{1-6}$ alkyl and $R^2$ is a H or $C_{1-6}$ alkyl.

8. A method of making the Formula IV compound or salt thereof, comprising the steps of:

a) ring closure and hydrogenation of (Formula IIa)

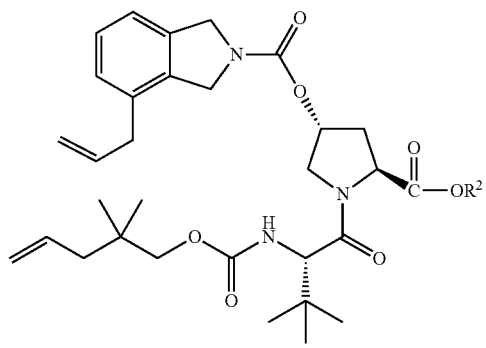

or salt thereof to form a compound of (Formula IV)

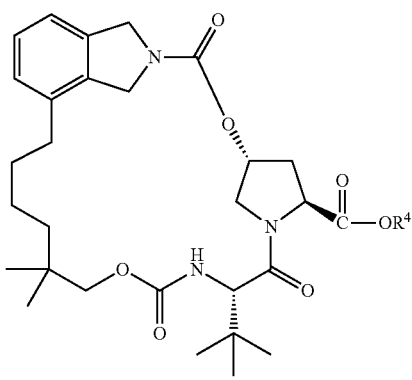

or salt thereof;

wherein $R^2$ and $R^4$ are either H, $C_{1-6}$ alkyl, $C_3$-$C_8$ cycloalkyl, or Aryl, provided that said Aryl is either phenyl, substituted phenyl, naphthyl, or substituted naphthyl, provided that substituted phenyl and substituted naphthyl each have 1 to 5 substituents independently selected from the group consisting of:

(1) $C_{1-6}$ alkyl,
(2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, $N(R^A)C(O)R^B$, $N(R^A)CO_2R_B$, $N(R^A)SO_2R^B$, $N(R^A)SO_2N(R^A)R^B$, $OC(O)N(R^A)R^B$, $N(R^A)C(O)N(R^A)R^B$, or $N(R^A)C(O)C(O)N(R^A)R^B$,
(3) O—$C_{1-6}$ alkyl,
(4) $C_{1-6}$ haloalkyl,
(5) O—$C_{1-6}$ haloalkyl,
(6) OH,
(7) halogen,
(8) CN,
(9) $NO_2$,
(10) $N(R^A)R^B$,
(11) $C(O)N(R^A)R^B$,
(12) $C(O)R^A$,
(13) C(O)—$C_{1-6}$ haloalkyl,
(14) $C(O)OR^A$,
(15) $OC(O)N(R^A)R^B$,
(16) $SR^A$,
(17) $S(O)R^A$,
(18) $SO_2R^A$,
(19) $SO_2N(R^A)R^B$,
(20) $N(R^A)SO_2R^B$,
(21) $N(R^A)SO_2N(R^A)R^B$,
(22) $N(R^A)C(O)R^B$,
(23) $N(R^A)C(O)N(R^A)R^B$,
(24) $N(R^A)C(O)C(O)N(R^A)R^B$, or
(25) $N(R^A)CO_2R^B$; and $R^A$ and $R^B$ are each independently H or $C_{1-6}$ alkyl.

9. A method of making (Compound A)

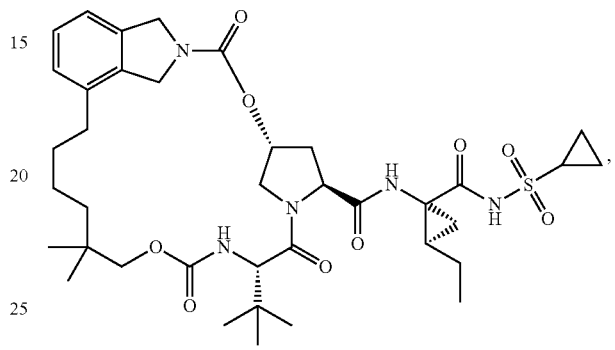

or a pharmaceutically acceptable salt thereof, comprising the steps of:

a) ring closure and hydrogenation of (Formula IIa)

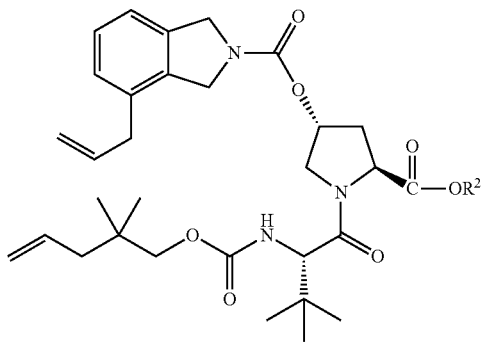

or salt thereof to form a compound of (Formula IV)

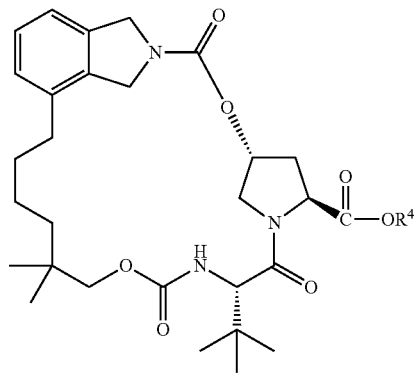

or salt thereof;

b) hydrolyzing the compound of Formula IV or salt thereof to form

63

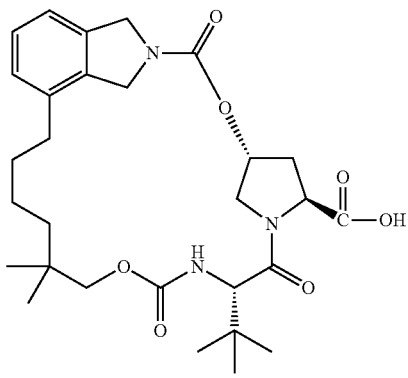

(Compound 11)

or salt thereof;
c) coupling Compound 11 or salt thereof to

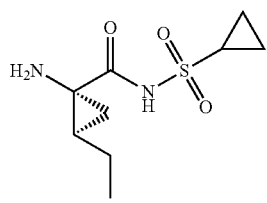

(Compound A-11)

or salt thereof, to form Compound A or salt thereof, and
d) optionally converting Compound A or salt thereof into a pharmaceutically acceptable salt;
wherein $R^2$ and $R^4$ are either H, $C_{1-6}$ alkyl, $C_3$-$C_8$ cycloalkyl, or Aryl, provided that said Aryl is either phenyl, substituted phenyl, naphthyl, or substituted naphthyl, provided that substituted phenyl and substituted naphthyl each have 1 to 5 substituents independently selected from the group consisting of:
(1) $C_{1-6}$ alkyl,
(2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, $N(R^A)C(O)R^B$, $N(R^A)CO_2R_B$, $N(R^A)SO_2R^B$, $N(R^A)SO_2N(R^A)R^B$, $OC(O)N(R^A)R^B$, $N(R^A)C(O)N(R^A)R^B$, or $N(R^A)C(O)C(O)N(R^A)R^B$,
(3) O—$C_{1-6}$ alkyl,
(4) $C_{1-6}$ haloalkyl,
(5) O—$C_{1-6}$ haloalkyl,
(6) OH,
(7) halogen,
(8) CN,
(9) $NO_2$,
(10) $N(R^A)R^B$,
(11) $C(O)N(R^A)R^B$,
(12) $C(O)R^A$,
(13) $C(O)$—$C_{1-6}$ haloalkyl,
(14) $C(O)OR^A$,
(15) $OC(O)N(R^a)R^B$,
(16) $SR^A$,
(17) $S(O)R^A$,
(18) $SO_2R^A$,
(19) $SO_2N(R^A)R^B$,
(20) $N(R^A)SO_2R^B$,
(21) $N(R^A)SO_2N(R^A)R^B$,
(22) $N(R^A)C(O)R^B$,

64

(23) $N(R^A)C(O)N(R^A)R^B$,
(24) $N(R^A)C(O)C(O)N(R^A)R^B$, or
(25) $N(R^A)CO_2R^B$; and
$R^A$ and $R^B$ are each independently H or $C_{1-6}$ alkyl.

10. The method of claim 9, wherein said Step C coupling is performed using EDC and pyridine or a pyridine derivative, wherein the pyridine derivative is

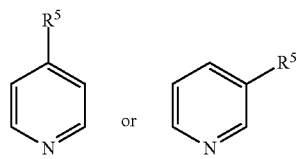

wherein $R^5$ is either hydrogen, Aryl, halogen, $C_{1-6}$ alkyl, O—$C_{1-6}$ alkyl or $C_3$-$C_8$ cycloalkyl.

11. The method of claim 8, wherein the compound of Formula IIa is a salt of:

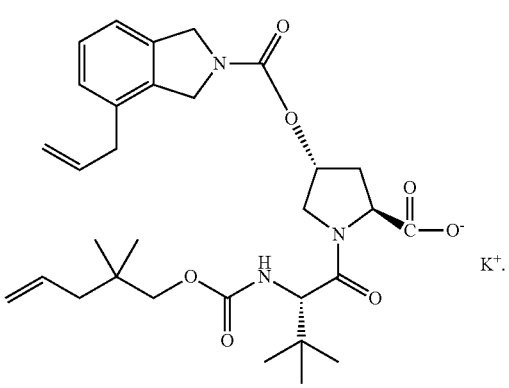 [SMILES: C=CCc1cccc2c1CN(C(=O)O[C@@H]1C[C@@H](C(=O)[O-])N(C(=O)[C@@H](NC(=O)OCC(C)(C)CC=C)C(C)(C)C)C1)C2]

12. The method of claim 8, wherein the compound of Formula IIa is:

[structure with $K^+$]

13. The method of claim 8, wherein $R^4$ is either H or $C_{1-6}$ alkyl.

14. The method of claim 8, further comprising the step of producing the compound of Formula IIa or salt thereof comprising the step of coupling

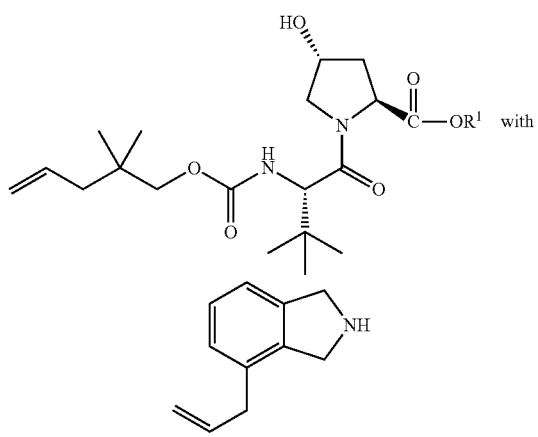

(Formula Ia)

or a salt thereof, wherein R¹ is either a $C_{1-6}$ alkyl, $C_3$-$C_8$ cycloalkyl, or Aryl.

15. The method of claim 14, further comprising the step of making the compound of Formula Ia by coupling

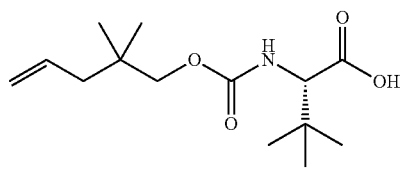 [SMILES: C=CCC(C)(C)COC(=O)N[C@H](C(=O)O)C(C)(C)C]

or salt thereof and

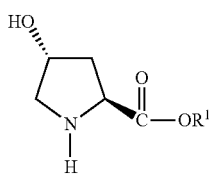

or salt thereof.

16. The method of claim 15, wherein

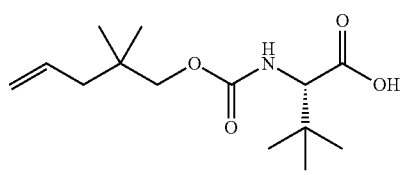 [SMILES: C=CCC(C)(C)COC(=O)N[C@H](C(=O)O)C(C)(C)C]

or salt thereof is

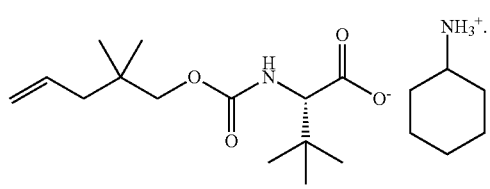 [SMILES: C=CCC(C)(C)COC(=O)N[C@H](C(=O)[O-])C(C)(C)C ; [NH3+]C1CCCCC1]

17. The method of claim 16, wherein R¹ is either H or $C_{1-6}$ alkyl.

18. The method of claim 17, wherein

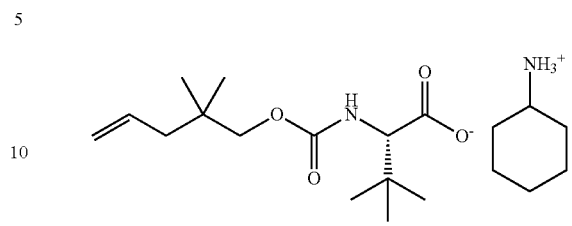

is made by a process comprising the following steps:

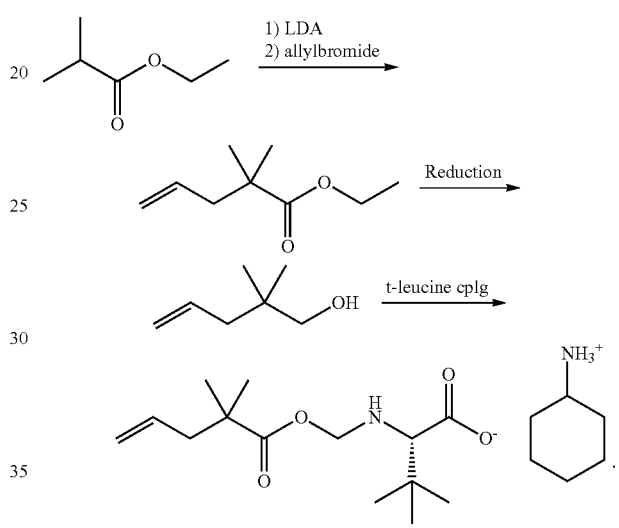

19. The method of claim 8, wherein said ring closure is performed by slow addition of catalyst and the compound of Formula IIa to a solvent at approximately the same time, wherein:

said solvent is provided at about 5-25 liters per Kg of substrate;

said catalyst is provided at a concentration of about 250 ml to 3 L per Kg of catalyst;

said compound is provided at a concentration of about 500 ml to 6 L per Kg of substrate; and said compound-solution, said catalyst-solution and said solvent are combined together over a period of 0.5-2.5 hrs.

20. The method of claim 9, where Compound A-11 or a salt thereof is produced by a process comprising the following steps:

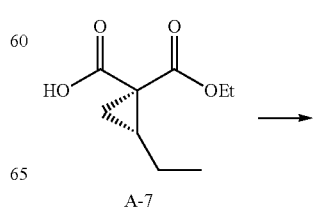

A-7